(12) United States Patent
Ley et al.

(10) Patent No.: US 10,206,958 B2
(45) Date of Patent: Feb. 19, 2019

(54) MODULATION OF FAT STORAGE IN A SUBJECT BY ALTERING POPULATION LEVELS OF CHRISTENSENELLACEAE IN THE GI TRACT

(71) Applicant: CORNELL UNIVERSITY, Ithaca, NY (US)

(72) Inventors: Ruth E. Ley, Ithaca, NY (US); Julia Goodrich, Ithaca, NY (US); Jillian Waters, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/305,496

(22) PCT Filed: Apr. 23, 2015

(86) PCT No.: PCT/US2015/027199
§ 371 (c)(1),
(2) Date: Oct. 20, 2016

(87) PCT Pub. No.: WO2015/164555
PCT Pub. Date: Oct. 29, 2015

(65) Prior Publication Data
US 2017/0042948 A1 Feb. 16, 2017

Related U.S. Application Data

(60) Provisional application No. 61/983,094, filed on Apr. 23, 2014.

(51) Int. Cl.
| | | |
|---|---|---|
| *A61K 35/741* | (2015.01) | |
| *A23L 33/135* | (2016.01) | |
| *A61K 9/19* | (2006.01) | |
| *A61K 35/00* | (2006.01) | |
| *A61K 35/74* | (2015.01) | |
| *A23L 33/00* | (2016.01) | |
| *A61K 9/00* | (2006.01) | |

(52) U.S. Cl.
CPC .......... *A61K 35/741* (2013.01); *A23L 33/135* (2016.08); *A23L 33/30* (2016.08); *A61K 9/0056* (2013.01); *A61K 9/19* (2013.01); *A61K 35/74* (2013.01); *A23V 2002/00* (2013.01); *A61K 2035/115* (2013.01)

(58) Field of Classification Search
CPC .............. A61K 2300/00; A61K 31/198; A61K 31/355; A61K 31/405; A61K 31/4415; A61K 31/519; A61K 31/59; A61K 33/06; A61K 33/24; A61K 33/30; A61K 31/202; A61K 35/20; A61K 2035/115; A61K 31/185; A61K 31/201; A61K 35/74; A61K 35/741; A61K 9/0056; A61K 9/19; A61K 38/17; A61K 31/00; A61K 31/575; A23V 2002/00; A23V 2200/332; A23V 2200/3204; A23V 2200/32; A23V 2200/328; A23V 2250/54246; A23V 2250/54252; A23L 33/18; A23L 33/135; A23L 33/19; A23L 33/30; A23L 1/3053; A23L 1/3056
See application file for complete search history.

(56) References Cited

U.S. PATENT DOCUMENTS

| | | |
|---|---|---|
| 2013/0224155 A1 | 8/2013 | Kaplan et al. |
| 2014/0045744 A1 | 2/2014 | Gordon et al. |

FOREIGN PATENT DOCUMENTS

| | | |
|---|---|---|
| WO | 2012/024638 A2 | 2/2012 |
| WO | 2014/019271 A1 | 2/2014 |
| WO | 2014/145958 A2 | 9/2014 |

OTHER PUBLICATIONS

Altschul S.F. et al., "Basic Local Alignment Search Tool", J. Mol. Biol. 215:403-410 (1990).
Altschul S.F. et al., "Gapped BLAST and PSI-BLAST: A New Generation of Protein Database Search Programs", Nucleic Acids Research 25(17):3389-3402 (1997).
Boker S. et al., "Openmx: An Open Source Extended Structural Equation Modeling Framework", Psychometrika 76(2):306-317 (Apr. 2011).
Desantis T.Z. et al., "Greengenes, a Chimera-Checked 16S rRNA Gene Database and Workbench Compatible with ARB", Applied and Environmental Microbiology 72(7):5069-5072 (Jul. 2006).
Ferrer M. et al., "Microbiota from the Distal Guts of Lean and Obese Adolescents Exhibit Partial Functional Redundancy Besides Clear Differences in Community Structure", Environmental Microbiology 15(1):211-226 (2013).
Gish W. et al., "Identification of Protein Coding Regions by Database Similarity Search", Nature Genetics 3:266-272 (Mar. 1993).
Harris J.K. et al., "New Perspective on Uncultured Bacterial Phylogenetic Division OP11", Applied and Environmental Microbiology 70(2):845-849 (Feb. 2004).
Huelsenbeck J.P. et al., "MRBAYES: Bayesian Inference of Phylogenetic Trees", Bioinformatics Applications Note 17(8):754-755 (2001).

(Continued)

*Primary Examiner* — Sarvamangala Devi
(74) *Attorney, Agent, or Firm* — Robin L. Teskin; LeClairRyan PLLC

(57) ABSTRACT

Disclosed herein are compositions that have substantially purified Christensenellaceae bacteria, and uses of these compositions to alter the microbiome of an individual. The addition of Christensenellaceae bacteria, such as *Christensenella*, to the microbiome of an individual can treat or prevent weight gain, reduce body weight, inhibit fat accumulation, reduce excess adiposity, and reduce a high body mass index (BMI), and can also treat or prevent conditions correlating with excess weight and fat and a high BMI, such as insulin sensitivity, metabolic syndrome, excess adiposity, and diabetes.

17 Claims, 5 Drawing Sheets
(5 of 5 Drawing Sheet(s) Filed in Color)
Specification includes a Sequence Listing.

(56) References Cited

OTHER PUBLICATIONS

Koenig J.E. et al., "Succession of Microbial Consortia in the Developing Infant Gut Microbiome", PNAS 108(Suppl. 1):4578-4585 (Mar. 15, 2011).

Ley R.E., "Obesity and the Human Microbiome", Current Opinion in Gastroenterology 26(1):5-11 (2010).

Madden T.L. et al., "Applications of Network BLAST Server", Methods in Enzymology 266:131-141 (1996).

Morotomi M. et al., "Description of *Christensenella minuta* gen. nov., sp. nov., Isolated from Human Faeces, Which Forms a Distinct Branch in the Order Clostridiales, and Proposal of Christensenellaceae fam. nov.", International Journal of Systematic and Evolutionary Micribiology 62:144-149 (2012).

Muegge B.D. et al., "Diet Drives Convergence in Gut Microbiome Functions Across Mammalian Phylogeny and Within Humans", Science 332:970-974 (May 20, 2011).

Papa E. et al., "Non-Invasive Mapping of the Gastrointestinal Microbiota Identities Children With Inflammatory Bowel Disease", PLoS One 7(6):e39242 (Jun. 2012).

Ronquist F. et al., "MrBayes 3: Bayesian Phylogenetic Inference Under Mixed Models", Bioinformatics Applications Note 19(12):1572-1574 (2003).

Xu M-Q et al., "Fecal Microbiota Transplantation Broadening its Application Beyond Intestinal Disorders", World J. Gastroenterol 21(1):102-111 (Jan. 7, 2015).

Zhang J. et al., "PowerBLAST: A New Network BLAST Application for Interactive or Automated Sequence Analysis and Annotation", Genome Research 7:649-656 (1997).

GenBank Accession No. AB490809.1 (1 page) (Jan. 17, 2012).

International Search Report dated Jul. 30, 2015 received in International Application No. PCT/US2015/027199.

Extended Supplementary European Search Report dated Aug. 16, 2017 received in European Patent Application No. 15 78 2372.5.

SEQUENCE LISTING

<160> NUMBER OF SEQ ID NOS: 8

<210> SEQ ID NO 1
<211> LENGTH: 1495
<212> TYPE: DNA
<213> ORGANISM: Christensenella minuta

<400> SEQUENCE: 1

```
ggctcaggac gaacgctggc ggcgtgctta acacatgcaa gtcgaacgag gttgcccttt      60
gtgaatcctt cgggaggaac tgtgggtata ccgagtggcg gacgggtgag taacgcgtga     120
gcaacctgcc ctgcaacggg ggacaacagt tggaaacgac tgctaatacc gcatgagacc     180
acgaaaccgc atggttttga ggtaaaagga tttattcgat gcaggatggg ctcgcgtccc     240
attagatagt tggtgaggta acggcccacc aagtcaacga tgggtagccg acctgagagg     300
gtgatcggcc acactggaac tgagacacgg tccagactcc tacgggaggc agcagtgggg     360
aatattgggc aatgggggaa accctgaccc agcaacgccg cgtgagggaa gaaggtcttc     420
ggattgtaaa cctttgtcct atgggacgaa agaaatgacg gtaccatagg aggaagctcc     480
ggctaactac gtgccagcag ccgcggtaat acgtagggag caagcgttgt ccggaattac     540
```

```
tgggcgtaaa gggtgcgtag gtggtcatgt aagtcagatg tgaaagaccg gggcttaacc      600
ccggggttgc atttgaaact gtgtgacttg agtacaggag agggaagtgg aattcctagt      660
gtagcggtga aatgcgtaga tattaggagg aacaccagtg gcgaaggcga ctttctggac      720
tgtaactgac actgaggcac gaaagcgtgg ggagcaaaca ggattagata ccctggtagt      780
ccacgccgta aacgatggat actaggtgtg gggcccgata gggttccgtg ccgaagcaaa      840
cgcattaagt atcccgcctg ggagtacga tcgcaaggtt gaaactcaaa ggaattgacg       900
ggggcccgca caagcagcgg agcatgtggt ttaattcgaa gcaacgcgaa gaaccttacc      960
aaggcttgac atcctctgac gactgtagag atacagtttc ccttcggggc agagagacag      1020
gtggtgcatg gttgtcgtca gctcgtgtcg tgagatgttg ggttaagtcc cgcaacgagc      1080
gcaacccttg ttgctagttg ccagcgcgta aggcgggaa ctctagtgag actgccgggg       1140
acaactcgga ggaaggtggg gacgacgtca aatcatcatg ccccttatgt cttgggctac      1200
acacgtgcta caatgccgg tacaaagggc agcgaacccg taaggggaag cgaatctcaa       1260
aaagccggtc ccagttcgga ttgtgggctg caacccgccc acatgaagtc ggagttgcta      1320
gtaatcgcga atcagcatgt cgcggtgaat gcgttcccgg gccttgtaca caccgcccgt     1380
cacaccacgg aagttgggag caccccgaagc cagtggctta accgtaagga gagagctgtc    1440
gaaggtgaga tcaatgactg gggtgaagtc gtaacaaggt agccgtatcg gaagg          1495

<210> SEQ ID NO 2
<211> LENGTH: 292
<212> TYPE: DNA
<213> ORGANISM: Christensenella minuta

<400> SEQUENCE: 2
gtgccagcag ccgcggtaat acgtagggag caagcgttgt ccggaattac tgggcgtaaa       60
gggtgcgtag gtggtcatgt aagtcagatg tgaaagaccg gggcttaacc ccggggttgc      120
atttgaaact gtgtgacttg agtacaggag agggaagtgg aattcctagt gtagcggtga      180
aatgcgtaga tattaggagg aacaccagtg gcgaaggcga ctttctggac tgtaactgac      240
actgaggcac gaaagcgtgg ggagcaaaca ggattagata ccctggtagt cc              292

<210> SEQ ID NO 3
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 3
gtgccagcmg ccgcggtaa                                                    19

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
taatctwtgg gvhcatcagg                                                   20

<210> SEQ ID NO 5
<211> LENGTH: 1357
<212> TYPE: DNA
```

```
<213> ORGANISM: Christensenella minuta
<220> FEATURE:
<221> NAME/KEY: misc_feature
<222> LOCATION: (550)..(554)
<223> OTHER INFORMATION: n is a, c, g, or t
<220> FEATURE:
<221> NAME/KEY: misc_feature
<222> LOCATION: (568)..(569)
<223> OTHER INFORMATION: n is a, c, g, or t
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (617)..(619)
<223> OTHER INFORMATION: n is a, c, g, or t

<400> SEQUENCE: 5
```

| | | | | | |
|---|---|---|---|---|---|
| ggacgaacgc | tggcggcgtg | cttaacacat | gcaagtcgaa | cgaggtgcag | cgagcggacc | 60 |
| ccttcgggga | gaagcatgct | gtatcctagt | ggcggacggg | tgagtaacgc | gtgagcaacc | 120 |
| tacccttgaa | tgggggacaa | cagctgggaaa | cggctgctaa | taccgcataa | gaccacgtca | 180 |
| tcgcatggtg | aagaggtaaa | aggattaatt | cgatcaagga | tgggctcgcg | tcccattaga | 240 |
| tagttggtga | gatagcagct | caccaagccg | acgatgggta | gccgacctga | gagggtgaac | 300 |
| ggccacactg | gaactgagac | acggtccaga | ctcctacggg | aggcagcagt | ggggaatatt | 360 |
| gggcaatggg | ggaaaccctg | acccagcaac | gccgcgtgaa | ggaagaaggc | cttcggttg | 420 |
| taaactttg | tcctatggga | cgaagaagtg | acggtaccat | aggaggaagc | tccggctaac | 480 |
| tacgtgccag | cagccgcggt | aatacgtagg | gagcgagcgt | tgtccggaat | tactgggcgt | 540 |
| aaagggtgcn | nnnncggaga | tgtaagtnng | gtgtgaaagc | ccggggctca | accccgggat | 600 |
| tgcanttgaa | antacannnc | ttgagtacag | gagaggcaag | tggaattcct | agtgtagcgg | 660 |
| tgaaatgcgt | agatattagg | aggaacacca | gtggcgaagg | cgacttgctg | gactgtaact | 720 |
| gacgctgagg | cacgaaagcg | tggggagcaa | acaggattag | ataccctggt | agtccacgcc | 780 |
| gtaaacgatg | gatactaggt | gtaggggtcg | ataggcctct | gtgccgaagc | aaacgcatta | 840 |
| agtatcccgc | ctgggagta | cgatcgcaag | gttgaaactc | aaaggaattg | acggggccc | 900 |
| gcacaagcag | cggagcatgt | ggtttaattc | gaagcaacgc | gaagaacctt | accaaggctt | 960 |
| gacatcctct | gacggctata | gagatatagc | ttcccttcgg | ggcagagaga | caggtggtgc | 1020 |
| atggttgtcg | tcagctcgtg | tcgtgagatg | ttgggttaag | tcccgcaacg | agcgcaaccc | 1080 |
| ttattgctag | ttgccagcac | gtaaaggtgg | gaactctagt | gagaccgccg | ggacaactc | 1140 |
| ggaggaaggt | ggggacgacg | tcaaatcatc | atgcccctta | tgtcttgggc | tacacacgtg | 1200 |
| ctacaatggc | cggtacaaag | ggtagcgaag | tcgtaagatg | aagcgaatct | caaaaagccg | 1260 |
| gtcccagttc | ggattgaggg | ctgcaacccg | ccctcatgaa | gtcggagttg | ctagtaatcg | 1320 |
| cgaatcagca | tgtcgcggtg | aatgcgttcc | cgggcct | | | 1357 |

```
<210> SEQ ID NO 6
<211> LENGTH: 1402
<212> TYPE: DNA
<213> ORGANISM: Christensenella minuta

<400> SEQUENCE: 6
```

| | | | | | |
|---|---|---|---|---|---|
| ttcgccctta | gagtttgatc | ctggctcagg | acgaacgctg | gcggcgtgct | taacacatgc | 60 |

```
aagtcgaacg aagttgctct ttgggaagcc ctcgggtgga actgtgagta tacttagtgg      120
cggacgggtg agtaacgcgt gagcaatctg ccctgcaatg ggggacaaca gttggaaacg      180
actgctaatg ccgcataaga ccacgaaacc gcatggttta gaggtaaaag gattcattcg      240
atgcaggata gctcgcgtc ccattagata gttggtgagg taacggccca ccaagtcaac       300
gatcggtagc cggactgaga ggttgaacgg ccacattggg actgagacac ggcccagact      360
cctacgggag gcagcagtgg ggaatattgc acaatggggg aaaccctgat gcagcgacgc      420
cgcgtggagg aagaaggtct tcggattgta aactcctgtt gttggggaag ataatgacgg      480
tgcccaacaa ggaagtgacg gctaactacg tgccagcagc cgcggtaata cgtagggagc      540
aagcgttgtc cggaattact gggcgtaaag ggtgcgtagg tggccatgta agtcaggtgt      600
gaaagaccgg ggctcaaccc cggggttgca cttgaaactg tgtggcttga gtacaggaga      660
gggaagtgga attcctagtg tagcggtgaa atgcgtagat attaggagga acaccagtgg      720
cgaaggcgac tttctggact gtaactgaca ctgaggcacg aaagcgtggg gagcaaacag      780
gattagatac cctggtagtc cacgccgtaa acgatggata ctaggtgtgg ggggcgata       840 gtcctccgtg ccgaagctaa cgcattaagt atcccgcctg gggagtacga tcgcaaggtt      900
gaaactcaaa ggaattgacg ggggcccgca caagcagcgg agcatgtggt ttaattcgaa      960
gcaacgcgaa gaaccttacc aaggcttgac atcctctgac gcatatagag atatatgttc     1020 ccttcgggc agagagacag gtggtgcatg gttgtcgtca gctcgtgtcg tgagatgttg      1080
ggttaagtcc cgcaacgagc gcaacccttg ttgctagttg ccagcacgta aggtgggaa      1140 ctctagtgag actgccgggg acaactcgga ggaaggtggg gacgacgtca atcatcatg     1200 ccccttatgt cttgggctac acacgtgcta caatggccgg tacaaagggc agcgacctcg     1260
taagagtaag cgaatctcaa aaagccggcc ccagttcgga ttgtgggctg caacccgccc     1320
acatgaagtc ggagttgcta gtaatcgcga atcagcatgt cgcggtgaat gcgttcccgg     1380
gccttgcaca caccgcccgt ca                                             1402

<210> SEQ ID NO 7
<211> LENGTH: 1497
<212> TYPE: DNA
<213> ORGANISM: Christensenella minuta

<400> SEQUENCE: 7
agagtttgat cctggctcag gacgaacgct ggcggcgtgc ttaacacatg caagtcgaac       60
gaagttgctc tttgggaagc cctcgggtgg aactgtgagt atacttagtg gcggacgggt      120
gagtaacgcg tgagcaatct gccctgcaat ggggacaac agttggaaac gactgctaat      180
accgcataag accacgaaac cgcatggttt agaggtaaaa ggattcattc gatgcaggat      240
gagctcgcgt cccattagat agttggtgag gtaacggccc accaagtcaa cgatgggtag      300
ccgacctgag agggtgatcg ccacattgg aactgagaaa cggtccaaac tcctacggga      360
ggcagcagtg gggaatattg gcaatggggg aaaccctga cccagcaacg ccgcgtgaag      420
gaagaaggcc ttcgggttgt aaactttgt cctatgggac gaaaaaatg acggtaccat       480 aggaggaagc tccggctaac tacgtgccag cagccgcgg aatacgtagg gagcaagcgt      540
tgtccggaat tactgggcgt aaagggtgcg taggtggcca tgtaagtcag gtgtgaaaga      600
ccggggctca accccgggt tgcacttgaa actgtgtggc ttgagtacag gagagggaag      660
tggaattcct agtgtagcgg tgaaatgcgt agatattagg aggaacacca gtggcgaagg      720
```

| | |
|---|---|
| cgactttctg gactgtaact gacactgagg cacgaaagcg tggggagcaa acaggattag | 780 |
| ataccctggt agtccacgcc gtaaacgatg gatactaggt gtggggggcg atagtcctcc | 840 |
| gtgccgaagc taacgcatta agtatcccgc ctggggagta cgatcgcaag gttgaaactc | 900 |
| aaaggaattg acggggggcccc gcacaagcag cggagcatgt ggtttaattc gaagcaacgc | 960 |
| gaagaacctt accaaggctt gacatcctct gacgcatata gagatatatg ttcccttcgg | 1020 |
| ggcagagaga caggtggtgc atggttgtcg tcagctcgtg tcgtgagatg tttgggttaag | 1080 |
| tcccgcaacg agcgcaaccc ttgttgctag ttgccagcac gtaaaggtgg gaactctagt | 1140 |
| gagactgccg gggacaactc ggaggaaggt ggggacgacg tcaaatcatc atgccccctta | 1200 |
| tgtcttgggc tacacacgtg ctacaatggc cggtacaaag gcagcgacc tcgtaagagt | 1260 |
| aagcgaatct caaaaagccg gccccagttc ggattgtggg ctgcaacccg cccacatgaa | 1320 |
| gtcggagttg ctagtaatcg cgaatcagca tgtcgcggtg aatgcgttcc cgggccttgt | 1380 |
| acacaccgcc cgtcacacca cggaagttgg gagcacccga agccagtggc ttaaccgtaa | 1440 |
| ggagagagct gtcgaaggtg agatcaatga ctggggtgaa gtcgtaacaa ggtaacc | 1497 |

```
<210> SEQ ID NO 8
<211> LENGTH: 1495
<212> TYPE: DNA
<213> ORGANISM: Christensenella minuta

<400> SEQUENCE: 8
```

| | |
|---|---|
| agagtttgat cctggctcag gacgaacgct ggcggcgtgc ttaacacatg caagtcgaac | 60 |
| gaagatgctc tttgtgaagc cttcgggtgg aactgtgagt agactgagtg gcggacgggt | 120 |
| gagtaacgcg tgagcaacct gccctgcaac ggggggacaac agctggaaac ggctgctaat | 180 |
| accgcataag accacggaat cgcatggttc tgaggtaaaa ggatttattc gatgcaggat | 240 |
| gggctcgcgt cccattagat agttggtgag gtaacggctc accaagtcaa cgatgggtag | 300 |
| ccgacctgag agggtgatcg gccacactgg aactgagaca cggtccagac tcctacggga | 360 |
| ggcagcagtg gggaatattg gcaakgggc gagcctgacc agcacgccgc gtgaaggaag | 420 |
| aaggccttcg ggttgtaaac ttttgtccta tgggaagaag aagtgacggt accataggag | 480 |
| gaagctccgg ctaactacgt gccagcagcc gcggtaatac gtagggagca agcgttgtcc | 540 |
| ggaattactg ggcgtaaagg gtgcgtaggc ggtttgacaa gtcagatgtg aaagcctggg | 600 |
| gcttaactcc aggattgcat ttgaaactgt aaacttgag tgcaggagag caagtggaa | 660 |
| ttcctagtgt agcggtgaaa tgcgtagata ttaggaggaa caccagtggc gaaggcgact | 720 |
| tgctggactg taactgacgc tgaagcacga aagcgtgggg agcaaacagg attagatacc | 780 |
| ctggtagtcc acgctgtaaa cgatggatac taggtgtagg gggcgatagt cttctgtgcc | 840 |
| gcagctaacg cattaagtat cccgcctggg gagtacgatc gcaaggttga aactcaaagg | 900 |
| aattgacggg ggcccgcaca agcagcggag catgtggttt aattcgaagc aacgcgaaga | 960 |
| accttaccaa ggcttgacat cctctgacgc atgtagagat acatgttccc ttcggggcag | 1020 |
| agagacaggt ggtgcatggt tgtcgtcagc tcgtgtcgtg agatgttggg ttaagtcccg | 1080 |
| caacgagcgc aacccttatt gctagttgcc agcacgtaaa ggtgggaact ctagtgagac | 1140 |
| cgccggggac aactcggagg aaggtgggga cgacgtcaaa tcatcatgcc cttatgtcct | 1200 |
| tgggctacac acgtgctaca atggccggta caaaggacag cgaacccgca agggggaagcg | 1260 |
| aatctcaaaa agccggtccc agttcggatt gagggctgca acccgccctc atgaagtcgg | 1320 |
| agttgctagt aatcgcgaat cagcatgtcg cggtgaatgc gttcccgggc cttgtacaca | 1380 |

```
ccgcccgtca caccacggaa gttgggagcg cccgaagcca gtggcttaac cgtaaggaga    1440
gagctgtcga aggtgagatc aatgactggg gtgaagtcgt aacaaggtaa ccgta         1495
```

MODULATION OF FAT STORAGE IN A SUBJECT BY ALTERING POPULATION LEVELS OF CHRISTENSENELLACEAE IN THE GI TRACT

CROSS-REFERENCE TO RELATED APPLICATIONS

This application claims priority to U.S. provisional application 61/983,094, filed Apr. 23, 2014, which is incorporated herein in its entirety.

STATEMENT REGARDING FEDERALLY SPONSORED RESEARCH OR DEVELOPMENT

This invention was made with Government support under Grant Numbers R01-DK093595-01 and 1DP2OD007444-01 awarded by NIH. The United States Government has certain rights in the invention.

INCORPORATION BY REFERENCE OF SEQUENCE LISTING

The Sequence Listing in the ASCII text file, named as 31024_6686_03_US_Sequence_Listing.txt of 12 KB, created on Oct. 19, 2016, and submitted to the United States Patent and Trademark Office via EFS-Web, is incorporated herein by reference.

BACKGROUND OF THE DISCLOSURE

The human gastrointestinal microbiome has been linked to metabolic disease and obesity; however, the relationship between host genetic variation and the diversity of gut microbiomes is largely unknown. Modification of the microbiome for therapeutic applications has the potential to treat a variety of disorders (Xu M Q et al., *World J. Gastroenterol.* 21:102-111(2015)). The enormous market for foods and supplements containing probiotic bacteria underscores the increasing public awareness of treatments involving introduction of beneficial bacteria to the gastrointestinal system.

Studies in humans and in animal models have shown that obesity is associated with a shift in the proportions of bacterial communities in the gut. Administration of the microbiota of obese individuals into the stomach of germ-free mice leads to greater weight gain in the recipient mice than in germ-free mice receiving microbiota from lean individuals, suggesting that microbial communities can predispose a host to weight gain or weight loss (Ley R E, *Curr. Opin. Gastroenterol.* 26:5-11(2010)). However, identification of bacteria associated with an obese or lean phenotype varies between studies. Understanding the interactions between a human host and the microbiome can lead to new treatments for a range of medical conditions by modifying the gut microbiome of a subject.

BRIEF SUMMARY OF THE DISCLOSURE

Disclosed herein are methods of inhibiting weight gain, promoting weight loss, or reducing adiposity in a subject, involving administering an effective amount of a composition of substantially purified Christensenellaceae bacteria to a subject in need. The Christensenellaceae can be bacteria of the genus *Christensenella*, such as *Christensenella minuta*, one or more species with the 16S rRNA gene sequence of any of SEQ ID NOS: 5-8, and mixtures thereof. In embodiments, at least 50% of the Christensenellaceae in the administered composition are viable. In other embodiments, the Christensenellaceae are lyophilized. In further embodiments, the composition has $10^6$ to $10^{12}$ colony forming units (CFUs) of Christensenellaceae bacteria.

Administration of the disclosed compositions increases the levels of Christensenellaceae, relative to the levels of other bacteria, in the gastrointestinal tract of a subject. The compositions can be administered on a daily or weekly basis. The subject to whom a composition of the invention is administered can have overweight, obesity, metabolic syndrome, and/or diabetes.

Further disclosed are methods of treating a condition in a subject selected from overweight, obesity, metabolic syndrome, excess adiposity, and diabetes. The methods include measuring the levels of Christensenellaceae in a biological sample from the subject; determining the amount of a composition of substantially purified Christensenellaceae to administer to the subject, based on the levels of Christensenellaceae in the sample; and administering a composition to the subject in an amount effective to treat the condition.

In some embodiments, a composition with Christensenellaceae is administered to a subject if the levels of Christensenellaceae in a biological sample from the subject are below 1.0% of the total abundance of bacteria in the sample. The sample can be selected from a fecal, intestinal, mucosal or oral sample.

The method can further include a step of measuring the levels of Christensenellaceae in a biological sample from the subject subsequent to administration of the composition, and repeating administration of the composition until the levels of *Christensenella* bacteria in the biological sample from the subject reach at least 1.0% of the total abundance of bacteria in the sample. The levels of Christensenellaceae can be measured by amplifying the 16S ribosomal ribonucleic acid (rRNA) gene from bacteria in the sample.

Further disclosed herein are compositions of substantially purified Christensenellaceae bacteria in a pharmaceutically acceptable carrier. In some embodiments, at least 50% of the Christensenellaceae in the composition are viable. In other embodiments, the Christensenellaceae bacteria in the composition are lyophilized. In further embodiments, the composition has $10^6$ to $10^{12}$ colony forming units (CFUs) of Christensenellaceae. In additional embodiments, the Christensenellaceae bacteria are *Christensenella* bacteria, such as *Christensenella minuta*, one or more species with the 16S rDNA sequence of any of SEQ ID NOS: 5-8, and mixtures thereof. The composition can be formulated as a tablet, capsule, oral liquid preparation, reconstitutable powder or suspension.

Further disclosed herein are foods and food or nutritional supplements containing a composition of substantially purified Christensenellaceae.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 3A-3F: Effects of Methanogen presence in donor stool. AB: Principal coordinates analysis of unweighted UniFrac distances for human fecal microbiota from obese and lean donors with and without methanogens before and after transplantation to germ-free mice. Symbols represent samples obtained from (i) the inoculum prior to transplantation, (ii) fecal samples at 4 time points, and (iii) cecal samples at Day 21. The symbols are colored according to the treatment group. Panel B shows PC3 plotted against PC2. The amount of variance described by the PCs is shown on the axes. C-E: Box plots showing concentrations of propionate (C), butyrate (D) and acetate (E) measured in the ceca of mice 21 days post-inoculation. Panel F shows box plots of gross energy content for dry stool collected at Day 12. Boxes with different letters adjacent to them have significantly different means, p<0.05. G: Percent weight change over time for germ-free mouse recipients. Donor stools were obtained from lean or obese donors with or without detectable Methanogens and did not include any donors used in the initial experiment (FIG. 2A). Mean values±S.E.M. For all panels, Dark blue=L+, lean donor with methanogens; Light blue=L−, lean donor lacking methanogens; Dark orange=O+, obese donor with methanogens; Light orange=O−, obese donor without methanogens.

DETAILED DESCRIPTION OF THE DISCLOSURE

Figure 1:
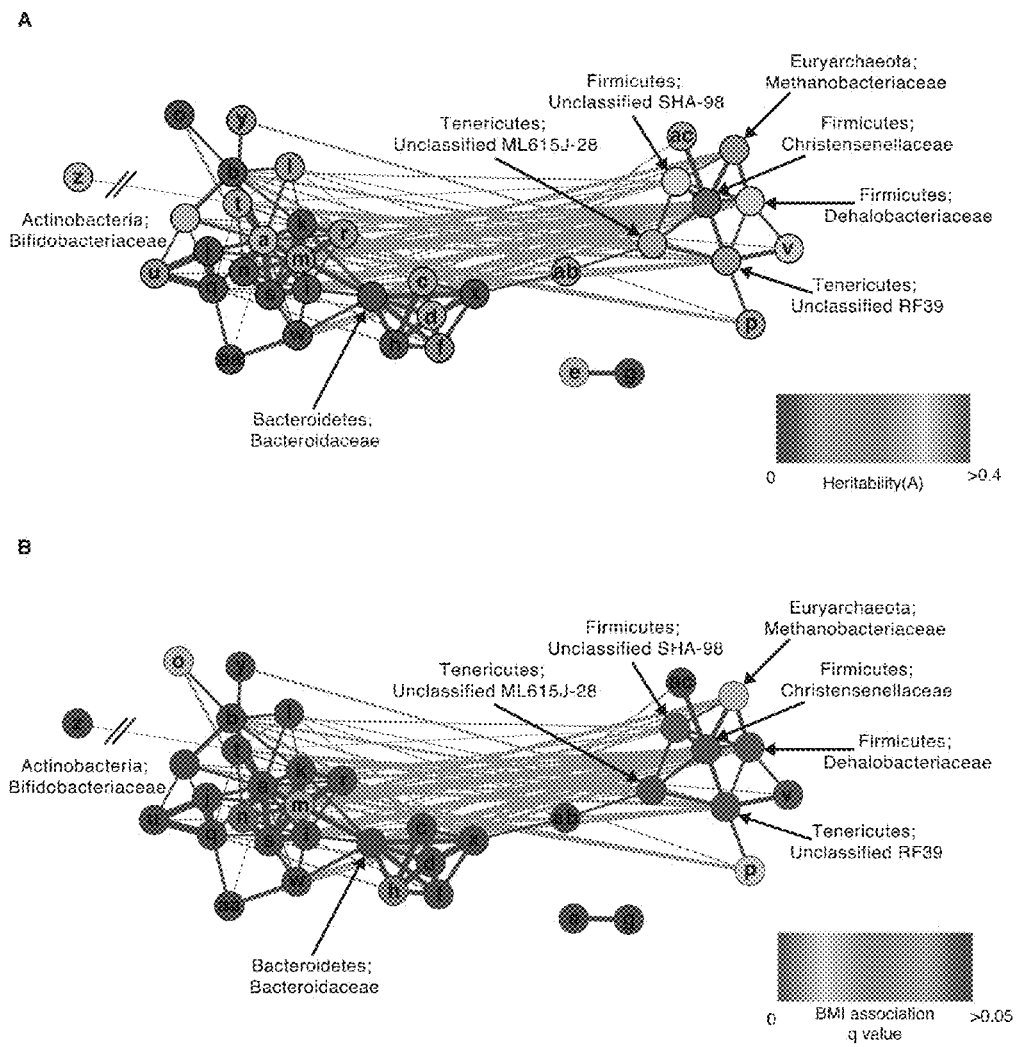
FIGS. 1A-1B. Christensenellaceae is the hub of a consortium of co-occurring heritable microbes that are associated with a lean BMI. A and B show the same network built from SparCC correlation coefficients between sequence abundances collapsed at the family level. The nodes represent families and the edges represent the correlation coefficients between families. Edges are colored blue for a positive correlation and grey for a negative correlation, and the weight of the edge reflects the strength of the correlation. Nodes are positioned using an edge-weighted force directed layout. In panel A, the nodes are colored by the heritability of the family, and in panel B, the nodes are colored by the significance of the association families and a normal vs. obese BMI. Family names are either indicated on the panel, or nodes are given a letter code. Phylum Actinobacteria: (a) Actinomycetaceae, (b) Coriobacteriaceae; Phylum Bacteroidetes: (c) Barnesiellaceae, (d) Odoribacteraceae, (e) Paraprevotellaceae, (f) Porphyromonadaceae, (g) Prevotellaceae, (h) Rikenellaceae; Phylum Firmicutes: (i) Carnobacteriaceae, (j) Clostridiaceae, (k) Erysipelotrichaceae, (l) Eubacteriaceae, (m) Lachnospiraceae, (n) Lactobacillaceae, (o) Mogibacteriaceae, (p) Peptococcaceae, (q) Peptostreptococcaceae, (r) Ruminococcaceae, (s) Streptococcaceae, (t) Tissierellaceae, (u) Turicibacteraceae, (v) Unclassified Clostridiales, (w) Veillonellaceae; Phylum Proteobacteria: (x) Alcaligenaceae, (y) Enterobacteriaceae, (z) Oxalobacteraceae, (aa) Pasteurellaceae, (ab) Unclassified RF32; Phylum Verrucomicrobia: (ac) Verrucomicrobiaceae.

Disclosed herein are compositions that have substantially purified bacteria of the family Christensenellaceae and/or the genus *Christensenella*, and uses of these compositions to alter the microbiome of an individual. The addition of Christensenellaceae to the microbiome of an individual can treat or prevent weight gain, reduce body weight, inhibit fat accumulation, reduce excess adiposity, and reduce a high body mass index (BMI), and can also treat or prevent conditions correlating with excess weight and fat and a high BMI, such as insulin sensitivity, metabolic syndrome, pre-diabetes and diabetes.

Christensenellaceae Bacteria

Christensenellaceae are a family of anaerobic bacteria of the order Clostridiales. Mulitple members of the Christensenellaceae, and multiple species of *Christensenella*, have been identified on the basis of homologous operational taxonomic unit (OTU) sequences in microbial phylogeny databases, such as Greengenes, a database of 16S RNA genetic sequences (DeSantis, T. Z., et al. *Appl Environ Microbiol* 72:5069-72 (2006)). An OTU as disclosed herein refers to a species or group of species identified on the basis of DNA sequence, specifically on the basis of 16S rRNA gene sequence. An OTU is considered a species-level OTU when the 16S rRNA gene sequence of the OTU has at least 97% identity to other species in a genus. In specific examples disclosed herein, OTUs are based on a percent identity of 97%. Bacterial/OTU sequences belonging to Christensenellaceae and *Christensenella* are publicly available, for example, in the Greengenes database at the Lawrence Berkeley National Laboratory website.

A bacterium can be defined as a member of the Christensenellaceae if (1) the 16S rRNA gene sequence of that bacterium shares at least 90%, 91%, 92%, 93%, 94%, 95%, 96%, 97%, 98%, 99%, or 100% identity, preferably 97% or greater identity, with any 16S rRNA gene sequence in a database of 16S rRNA gene sequences, such as the Greengenes database that has the taxonomic classification of Christensenellaceae, or (2) a phylogenetic analysis reveals that the 16S rRNA gene sequence of that bacterium is most closely related to the 16S rRNA gene sequence of a member of the Christensenellaceae, such that this sequence and a sequence from a member of the Christensenellaceae share a common ancestor sequence that is unique to the family Christensenellaceae (and members of other families do not share that ancestor). Phylogenetic analysis approaches that are acceptable as general practice in the field of microbiology for 16S rRNA gene phylogenetics include: (a) a multiple sequence alignment of the 16S rRNA gene sequences (members of the Christensenellaceae+the novel sequence+non-Christensenellaceae) using secondary structure information, followed by (b) use of either the General-Time reversible model of evolution in a Maximum Likelihood (ML) analysis with bootstrapping (Harris, J. K., et al., *Appl. Environ. Microbiol.* 70:845-849 (2004)), or a Bayesian phylogenetics analysis (Huelsenbeck, J. P. and F. Ronquist, *Bioinformatics* 17:754-755 (2001). Ronquist, F. and J. P. Huelsenbeck, *Bioinformatics* 19:1572-1574 (2003)). These tools are commonly available and implemented in many different standard sequence analysis software packages. Visualization of resulting phylogenetic trees can be performed software available in the art for phylogenetic tree visualization. For inclusion in the family Christensenellaceae, the bootstrap support in an ML analysis is 70%, or a 70% probability for a Bayesian analysis.

*Christensenella* is a recently identified genus of the Christensenellaceae. The first isolated species of *Christensenella* was *Christensenella minuta*, which was isolated from a human fecal sample (Morotomi, et al., *Int. J. Syst. Evol. Microbiol.* 62:144-149 (2012). *C. minuta* has a 16S ribosomal RNA gene sequence of SEQ ID NO: 1. The *C. minuta* 16S rRNA sequence is identified by Genbank Accession No. AB490809.

Bacteria belonging to Christensenellaceae and *Christensenella* can be identified by amplifying the 16S rRNA gene from a sample. PCR primers that amplify universally conserved regions of the 16S rRNA gene are known in the art. For example, using the known 16S rRNA gene primers 515F (SEQ ID NO: 3) and 806R (SEQ ID NO: 4) to amplify the 16S rRNA gene sequence from *Christensenella minuta* amplifies a portion of SEQ ID NO: 1 disclosed herein as SEQ ID NO: 2. A bacterium belonging to the *Christensenella* genus is identified as having a 16S RNA gene sequence with at least 90%, 91%, 92%, 93%, 94%, 95%, 96%, 97%, 98%, or 99% identity to the sequence of SEQ ID NO: 1 or SEQ ID NO: 2. Additional 16S sequences for bacteria within the genus of *Christensenella* are provided as SEQ ID NOS: 5-8 (OTU numbers 701845, 177179, 1146771, and 361793 in the Greengenes database, respectively). The identity of each sequence relative to SEQ ID NO: 1 is as follows: SEQ ID NO: 5, 93% identity to SEQ ID NO: 1; SEQ ID NO: 6, 95% identity to SEQ ID NO: 1; SEQ ID NO: 7, 97% identity to SEQ ID NO: 1; SEQ ID NO: 8, 95% identity to SEQ ID NO: 1.

"Identity", as used herein, indicates that at any particular position in the aligned sequences, the homologous nucleotide is the same between the sequences. Degrees of identity and similarity can be readily calculated, using, for example, the BLAST™ software available from the National Center for Biotechnology Information (NCBI) (Altschul, S. F. et al., 1990, *J. Mol. Biol.* 215:403-410; Gish, W. & States, D. J. 1993, *Nature Genet.* 3:266-272. Madden, T. L. et al., 1996, *Meth. Enzymol.* 266:131-141; Altschul, S. F. et al., 1997, *Nucleic Acids Res.* 25:3389-3402; Zhang, J. & Madden, T. L. 1997, *Genome Res.* 7:649-656).

Compositions of Purified Christensenellaceae and *Christensenella* Bacteria

Disclosed herein are compositions of substantially purified bacteria of the family Christensenellaceae and the genus *Christensenella*. A composition of "substantially purified Christensenellaceae bacteria" means that at least 75%, 80%, 85%, 90%, 95%, 98%, 99% or more of the bacterial cells present in the composition belong to the family Christensenellaceae. A composition of "substantially purified *Christensenella* bacteria" means that at least 75%, 80%, 85%, 90%, 95%, 98%, 99% or more of the bacterial cells present in the composition belong to the genus *Christensenella*. The terms "isolated" and "purified" are used interchangeably herein to refer to a material that is substantially or essentially removed from or concentrated in its natural environment. For example, a cell is isolated if it is substantially removed from other endogenous cell types, tissues, and materials which the cell would normally be found in proximity to in a subject. Methods for purification and isolation of cell types according to expression of cell-surface markers are documented methodologies.

In one embodiment, the Christensenellaceae are bacteria of the genus *Christensenella*. In a further embodiment, the *Christensenella* bacteria are selected from *Christensenella minuta*, one or more *Christensenella* species with the 16S sequence of any of SEQ ID NOS: 5-8, and mixtures thereof. In a specific example, the bacteria are *C. minuta* bacteria.

In one example, at least 50%, 55%, 60%, 65%, 70%, 75%, 80%, 85%, 90%, 95%, 98%, or 99% of Christensenellaceae or *Christensenella* bacteria in the disclosed composition are viable. A "viable" bacterium is capable of forming a colony, for example, under conditions suitable for growth of said bacterium. A viable bacterium is also referred to herein as a colony forming unit (CFU).

Christensenellaceae and *Christensenella* can be cultured under anaerobic conditions using, for example, the methods disclosed in Morotomi, et al. (*Int. J. Syst. Evol. Microbiol.* 62:144-149 (2012)). For example, cultures may be inoculated into tubes or plates for growth in anaerobic conditions at 32-42° C., preferably 37° C., with a culture medium of modified Gifu anaerobic medium (GAM broth; Nissui Pharmaceutical) containing 1%-2%, preferably 1.5% (w/v) agar supplemented with 2-8% bile (Bacto oxgall; Difco) and NaCl. As another example, *Christensenella* can be cultured in brain heart infusion broth supplemented with yeast (2-8 g/l, preferably 5 g/l), menadione (0.5-2.0 mg/l, preferably 1.0 g/l), hemin (5-15 mg/l, preferably 10 mg/l), and L-cysteine-HCL (0.2-0.8 g/l, preferably 0.5 g/l) at 32-42° C., preferably 37° C., under anaerobic conditions.

In another example, the composition includes lyophilized Christensenellaceae or *Christensenella* bacteria. Lyophilized compositions of the inventions still contain at least 50%, 55%, 60%, 65%, 70%, 75%, 80%, 85%, 90%, 95%, 98%, or 99% viable Christensenellaceae or *Christensenella* bacteria.

In a further example, the composition contains about $10^6$ to $10^{12}$ CFU of bacteria/g of support, and more particularly from $10^8$ to $10^{11}$ CFU of bacteria/g of support of Christensenellaceae or *Christensenella* bacteria. By support is meant the food product or the pharmaceutically acceptable excipient.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

Bacteria and strains of the family Christensenellaceae, and bacteria and strains of the genus *Christensenella*, are probiotic. Generally, by a probiotic bacterium or strain it is meant a non-pathogenic microorganism which, when ingested live, exercises a beneficial effect on the host's health. These probiotic strains generally have the ability to survive the passage through the upper part of the digestive tract. Without being limited, it is thought that these bacteria can exercise their beneficial effect on health on the one hand via ecological interactions with the resident flora in the digestive tract (i.e., the "gut microbiome"), and on the other hand via their ability to influence various aspects of the host physiology. These bacteria, when given in a sufficient number, have the ability to progress live through the intestine, however they do not cross the intestinal barrier and their primary effects are therefore induced in the lumen and/or the wall of the gastrointestinal tract. They then form part of the resident flora during the administration period and ideally on an extended basis subsequent to administration. This colonization (or transient colonization) allows the probiotic bacteria to exercise a beneficial effect both through interactions with the gut microbiome and on the host itself.

Compositions disclosed herein can include substantially purified Christensenellaceae or *Christensenella* bacteria and one or more acceptable excipients. Examples of acceptable excipients include: sugars such as sucrose, isomerised sugar, glucose, fructose, palatinose, trehalose, lactose and xylose; microcrystalline cellulose and other celluloses, lactose, sodium citrate, calcium carbonate, dibasic calcium phosphate, glycine, starch, milk sugar and high molecular weight polyethylene glycols; emulsifiers such as sucrose esters of fatty acids, glycerin esters of fatty acids and lecithin; thickeners (stabilizers) such as carrageenan, xanthan gum, guar gum, pectin and locust bean gum; acidifiers such as citric acid, lactic acid and malic acid; fruit juices such as lemon juice, orange juice and berry juice; vitamins such as vitamin A, vitamin B, vitamin C, vitamin D and vitamin E; and minerals such as calcium, iron, manganese and zinc.

Compositions of the invention may be prepared by admixture, usually adapted for oral administration. Such compositions may be in the form of tablets, capsules, oral liquid preparations, conventional food products, powders, granules, lozenges, reconstitutable powders or suspensions.

Tablets and capsules for oral administration can also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; and lubricating agents such as magnesium stearate, stearic acid, glyceryl behenate and talc.

Oral liquid preparations may be in the form of, for example, aqueous or oily suspensions, solutions, emulsions, syrups or elixirs, or may be in the form of a dry product for reconstitution with water or another suitable vehicle before use. Such liquid preparations may contain conventional additives such as suspending agents, emulsifying agents, non-aqueous vehicles (which may include edible oils), preservatives, and if desired, conventional flavorings or colorants.

Further disclosed herein is a food, food or nutritional supplement containing a composition of the invention, such as a dairy based product (e.g. fermented milk, vegetable milk, soybean milk, butter, cheese or yoghurt) or fruit juice. The composition can be formulated as a food or drink for adult and/or infant humans and/or animals. The composition can be a probiotic composition.

Methods of Inhibiting Weight Gain or Promoting Weight Loss

Further disclosed herein are methods of inhibiting weight gain, promoting weight loss, and reducing excess adiposity in a subject. The methods include administering an effective amount of a composition of substantially purified Christensenellaceae bacteria to a subject in need of weight gain inhibition or weight loss. In one example, the Christensenellaceae bacteria are *Christensenella* bacteria.

A subject in need of weight gain inhibition is defined as a subject with a body mass index (BMI) of 24 or greater. A subject in need of weight loss is defined as a subject with a BMI of 25 or greater. BMI (calculated as weight in kilograms divided by the square of height in meters) is the most commonly accepted measurement for overweight and/or obesity. A BMI exceeding 25 is considered overweight, while obesity is defined as a BMI of 30 or more, with a BMI of 35 or more considered as serious comorbidity and a BMI of 40 or more considered morbid obesity. Thus, for example, a subject with a BMI of 24 is in need of weight gain inhibition, while a subject with a BMI of 25 or greater is in need of both weight loss, and inhibition from further weight gain.

Excess adiposity is defined as having a body fat weight % (fat weight/total weight) of greater than 25% in men, or 30% in women. Adiposity can be measured, for example, by air-displacement plethysmography, bioelectrical impedance analysis, dual energy X-ray absorptiometry, hydrostatic weighing, isotope dilution, or skin fold measurements. Body fat percentage can be estimated from a person's BMI by the following formula: (1.2×BMI)+(0.23×age) 5.4 (10.8×gender) where gender=0 for women, 1 for men.

Administration of the compositions disclosed herein increases the levels of Christensenellaceae in the gastrointestinal tract of a subject, relative to the levels of other bacteria in the gastrointestinal tract of the subject. By "levels" is meant the relative abundance of Christensenellaceae relative to the abundance of other bacteria in the gastrointestinal tract of the subject, or the relative ratio of Christensenellaceae, relative to the ratio of other bacteria in the gastrointestinal tract of the subject.

The inventors have determined that the presence of Christensenellaceae and *Christensenella* bacteria affects the abundances of multiple types of bacteria in the gut microbiome, which, without being limited, is considered to have a positive effect on a subject's weight and adiposity. For example, treatment with or administration of a composition disclosed herein can increase the levels of Christensenellaceae bacteria at the family level, including increasing the level of one or more species of the genus *Christensenella*. As another example, treatment with or administration of a composition disclosed herein can increase the levels of other beneficial or probiotic bacteria, such as bacteria of the genus *Oscillospira*, bacteria of the family Rikenellaceae and/or the family Erysipelotrichaceae, and/or archaea such as of the class Methanobacteria or the order Methanobacteriales. The inventors have determined that the Christensenellaceae are the central "hub" of a cluster of beneficial bacterial families associated with a healthy body weight and a healthy BMI. Thus, without being limited, it is believed that altering the levels of Christensenellaceae, by administration of a composition of a single species, a mixture of two or more species of the family Christensenellaceae, or a mixture of two or more species of *Christensenella*, positively influences or reshapes the gut microbiome and creates a gastrointestinal environment that assists a subject with weight loss, prevents or retards weight gain, and/or reduces excess adiposity in the subject.

The methods disclosed herein include administration of a dosage of from about $10^6$ to $10^{12}$ CFU of Christensenellaceae or *Christensenella* bacteria/dose, and more particularly from $10^8$ to $10^{11}$ CFU of Christensenellaceae or *Christensenella* bacteria/dose. By the term "per dose" it is meant that this amount of microorganism is provided to a subject either per day or per intake. For example, if the microorganism is to be administered in a food support (for example in a yogurt)—then the yogurt can contain from about $10^6$ to $10^{12}$ CFU Christensenellaceae or *Christensenella* bacteria. Alternatively, however, this amount of microorganism may be split into multiple administrations each consisting of a smaller amount of microbial loading—so long as the overall amount of microorganism received by the subject in any specific time (for instance each 24 h period) is from about $10^6$ to $10^{12}$ CFU of Christensenellaceae or *Christensenella* bacteria, preferably $10^8$ to $10^{11}$ CFU of Christensenellaceae or *Christensenella* bacteria.

Methods of Treatment

Further disclosed are methods of treating a condition selected from overweight, obesity, metabolic syndrome, excess adiposity, or diabetes in a subject. The methods include measuring the levels of Christensenellaceae in a biological sample from a subject; determining the amount of a composition of substantially purified Christensenellaceae to administer to the subject, based on the levels of Christensenellaceae in said sample; and administering a composition to the subject in an amount effective to treat the condition.

The term "subject", as used herein, means an animal. Preferably, the subject is a mammal, including for example livestock (including cattle, horses, pigs, chickens and sheep), or humans. In some aspects of the present invention the animal is a companion animal (including pets), such as a dog or a cat. In a specific example, the subject is a human.

Overweight and obese individuals frequently suffer from weight-related disorders such as insulin resistance, diabetes, including type 2 diabetes, and dyslipidemia. These individuals also frequently suffer from hypertension, increased risk for cardiovascular diseases such as atherosclerosis and coronary heart disease. Other health conditions caused or exacerbated by overweight and obesity include sleep apnea, obesity-related hypoventilation, back and joint problems, non-alcoholic fatty liver disease and gastroesophageal reflux disease.

Metabolic syndrome is characterized by the presence of three or more of these components: an elevated waist circumference in men of equal to or greater than 40 inches (102 cm); an elevated waist circumference in women of equal to or greater than 35 inches (88 cm); elevated triglycerides of equal to or greater than 150 mg/dL; reduced HDL ("good") cholesterol in men of less than 40 mg/dL, or less than 50 mg/dL in women; elevated blood pressure of equal to or greater than 130/85 mm Hg; and elevated fasting glucose equal to or greater than 100 mg/dL.

Diabetes mellitus, often simply referred to as diabetes, is a condition in which a person has a high blood sugar (glucose) level, either because the body doesn't produce enough insulin, or because body cells don't properly respond to the insulin that is produced. Diabetes can be diagnosed, for example, from an oral glucose tolerance test as a 2-hour plasma glucose concentration of greater than or equal to 200 mg/dl. Insulin is a hormone produced in the pancreas that enables body cells to absorb glucose, to turn into energy. If the body cells do not absorb the glucose, the glucose accumulates in the blood (hyperglycemia), leading to vascular, nerve, and other complications. Type 1 diabetes results from the body's failure to produce insulin, and presently requires the person to inject insulin. Type 2 diabetes results from insulin resistance, a condition in which cells fail to use insulin properly, sometimes combined with an absolute insulin deficiency.

The single greatest risk factor for developing type 2 diabetes is being overweight or obese. Almost 90% of people living with type 2 diabetes are overweight or obese. People who are overweight or obese have added pressure on their body's ability to use insulin to properly control blood sugar levels, and are therefore more likely to develop diabetes.

As used herein, "treatment" refers to clinical intervention in an attempt to alter the disease course of the individual or cell being treated, and can be performed during the course of clinical pathology. Therapeutic effects of treatment include without limitation, preventing recurrence of disease, alleviation of symptoms, diminishment of any direct or indirect pathological consequences of the disease, decreasing the rate of disease progression, amelioration or palliation of the disease state, and remission or improved prognosis.

As used herein, the terms "therapeutically effective amount" and "effective amount" are used interchangeably to refer to an amount of a composition of the invention that is sufficient to result in the prevention of the development or onset of overweight, obesity, metabolic disorder, diabetes, or one or more symptoms of the particular condition being treated, to enhance or improve the effect(s) of another therapy, and/or to ameliorate one or more symptoms of overweight, obesity, metabolic disorder, or diabetes. In one example, an effective amount is an amount that aids in reduction of weight in the subject.

A therapeutically effective amount can be administered to a patient in one or more doses sufficient to palliate, ameliorate, stabilize, reverse or slow the progression of the disease, or otherwise reduce the pathological consequences of the disease, or reduce the symptoms of the disease. The amelioration or reduction need not be permanent, but can be for a period of time ranging from at least one hour, at least one day, or at least one week or more. The effective amount is generally determined by the physician on a case-by-case basis and is within the skill of one in the art. Several factors are typically taken into account when determining an appropriate dosage to achieve an effective amount. These factors include age, sex and weight of the patient, the condition being treated, the severity of the condition, as well as the route of administration, dosage form and regimen and the desired result.

Measuring Levels of Christensenellaceae in a Sample

The levels of Christensenellaceae and/or *Christensenella* can be measured by amplifying the 16S rRNA gene from bacteria in a sample. As used herein, the term "amplifying" also encompasses "sequencing" to determine the variety of bacterial genera and species present in a sample. The sample can be a fecal, intestinal, mucosal or oral sample. Preferred samples are fecal samples.

In one example, the levels of Christensenellaceae and/or *Christensenella* are measured in a sample by performing quantitative PCR using primers that specifically amplify members of the family or of the genus, and these levels are normalized to the total 16S rRNA in a sample. The prevalent strategy for amplifying the 16S rRNA gene from microorganisms in a sample involves utilizing probes and primers that anneal to conserved regions at the edges of known variable domains in the 16S rRNA gene sequence, for amplification and sequencing across the variable domains to identify species-specific variable sequences and thus identify species within the sample. Typically, primer pairs have been designed to amplify a single variable ("V") region, such as the 16S V3, V4, or V5 region. Common primers to amplify the V4 region include universal 16S primers 515F (SEQ ID NO: 3) and 806R (SEQ ID NO: 4).

Traditional amplification methods such as Sanger sequencing, or next generation sequencing methods, are suitable for amplification and sequencing of microorganisms. However, given the potentially large number and variety of microorganisms which can be present in a given sample, high-throughput/next generation sequencing methods, which are capable of rapidly generating large amounts of sequence data, are particularly well suited for the rapid and accurate identification of microorganisms in a sample. "Next generation" sequencing technologies enable a large number of distinct nucleic acid sequences to be sequenced simultaneously and at a high density. Such sequencing technologies include, but are not limited to, sequencing-by-synthesis (e.g., Illumina dye sequencing; Single Molecule Real Time Sequencing platform by Pacific Biosciences); sequencing by ligation (SOLiD or Polony sequencing platform, Applied Biosystems); pyrosequencing (454 Sequencing, Roche Diagnostics); and ion semiconductor sequencing (Ion Torrent Sequencing, Life Technologies).

PCR amplicons can be purified, for example using a magnetic bead system, and quantified, using commercially available products for purification and quantification. DNA can be sequenced and analyzed using any one of several sequencing platforms, such as an Illumina MISEQ platform (Illumina Inc., San Diego, Calif., USA).

Once the 16S rRNA gene in a sample has been amplified and sequenced, microorganisms present in the sample are then identified based on identification of species-specific 16S DNA amplicon sequences generated from the sample. Quality filtering (to remove "noise" generated by random sequencing errors) and analysis of 16S rRNA gene sequence data can be performed using publicly available bioinformatic analytic tools for taxon identification from raw DNA sequencing data, such as the Quantitative Insights Into Microbial Ecology (QIIME) analytic tool (Caporaso et al., *Nature Methods* 7:335-336 (2010)).

As disclosed elsewhere in this application, Christensenellaceae bacteria are identified based on (1) at least 90%, 91%, 92%, 93%, 94%, 95%, 96%, 97%, 98%, 99%, or 100% identity, preferably 97% identity or greater, of the 16S rRNA gene sequence or sequences of the bacteria with Christensenellaceae 16S rRNA gene sequences, using an available database of 16S rRNA gene sequences, or (2) phylogenetic analysis of the 16S rRNA gene sequence of the bacteria identifying the bacteria as Christensenellaceae, using known methods for determining phylogeny. The levels of Christensenellaceae in a sample can be determined by comparing the abundance or ratio of sequences identified as Christensenellaceae to the total bacterial abundance in a sample, or to the abundance or ratio of sequences identified as not belonging to Christensenellaceae. Alternatively, the abundance or ratio of Christensenellaceae in a sample, relative to other bacterial species, can be measured by use of analytic tools, such as QIIME. These tools can generate taxonomic distributions in a sample by comparing the bacterial 16S rRNA gene sequences from the sample to the 16S rRNA gene sequences in a database such as Greengenes, which have previously been assigned taxonomic classifications. *Christensenella* bacteria are identified based on at least 90%, 91%, 92%, 93%, 94%, 95%, 96%, 97%, 98%, or 99% identity to the sequence of SEQ ID NO: 1 or SEQ ID NO: 2 (the portion of SEQ ID NO: 1 generated by amplification with the 515F and 806R universal 16S primers). Thus, the levels of *Christensenella* in a sample can be measured by comparing the abundance or ratio of sequences having at least 90% identity to SEQ ID NO: 1 or SEQ ID NO: 2 to the abundance or ratio of sequences falling outside of this range. Alternatively, the abundance or ratio or *Christensenella* in a sample, relative to other bacterial species, can be measured by use of analytic tools, such as QIIME, to generate taxonomic distributions in a sample by comparing the bacterial 16S rRNA gene sequences from the sample to the 16S rRNA gene sequences in a database such as Greengenes, which have previously been assigned taxonomic classifications.

In one example, if the relative abundance of Christensenellaceae in a sample from a subject is less than 0.01 (out of a total bacterial abundance=1), or if the ratio or level of Christensenellaceae in the sample is below 1.0% of the total bacteria in the sample, the subject is diagnosed with low levels of Christensenellaceae. Accordingly, the subject can benefit by administration of a composition as disclosed herein. The subject can be treated by administration of a dosage of from about $10^6$ to $10^{12}$ CFU of Christensenellaceae or *Christensenella* bacteria/dose, and more particularly from $10^8$ to $10^{11}$ CFU of Christensenellaceae or *Christensenella* bacteria/dose. Where the subject has abundance levels below $0.6 \times 10^{-3}$ Christensenellaceae, the subject is preferably administered a dosage on a daily or twice daily basis.

In another example, if the relative abundance of Christensenella in a sample from a subject is less than $4.8 \times 10^{-5}$ (out of a total bacterial abundance=1), or if the ratio or level of Christensenella bacteria in the sample is below $4.8 \times 10^{-3}$% of the total bacteria in the sample, the subject is diagnosed with low levels of Christensenella. Accordingly, the subject can benefit by administration of a composition as disclosed herein. The subject can be treated by administration of a dosage of from about $10^6$ to $10^{12}$ CFU of Christensenella bacteria/dose, and more particularly from $10^8$ to $10^{11}$ CFU of Christensenella bacteria/dose. Where the subject has abundance levels below $4.4 \times 10^{-5}$ Christensenella, the subject is preferably administered a dosage on a daily or twice daily basis.

In another example, the levels of Christensenellaceae and Christensenella are determined by measuring the relative abundance of 16S rRNA genes belonging to these taxa in a set of 16S rRNA gene sequences derived from a sample, either by PCR and sequencing of 16S rRNA genes using universal primers designed to target a wide diversity of microbiota, or by metagenomic sequencing of the sample, wherein random DNA segments are sequenced and classified as belonging to the genomes of specific bacteria.

When sequencing the gut microbiota of an individual, a higher sequencing depth (meaning more counts of 16S rRNA), increases the accuracy of representation of microbes in the gut and the relative abundance of bacterial taxa to one another. Sequencing depth refers to the amount of sequence generated per sample, where greater depth corresponds to more sequences generated. Rare taxa (those at extremely low abundances) can be missed if a sample is sequenced with less depth, simply because based on probability of amplifying that sequence. The more sequences that are generated, the more accurate the estimates for all taxa, including the taxa that are not the most abundant. For example, for a sample containing $10^{10}$ microbial cells, a sequencing depth of 30,000-100,000 sequences provides a small fraction that is representative of a community with many more cells.

In analyses of sequences generated by 16S rRNA gene PCR and sequencing, the inventors observed that sequences belonging to the family Christensenellaceae are on average more abundant in a sample than sequences belonging to the genus Christensenella, and are found in most individuals (96% of those samples). The inventors have further observed that the relative abundance of Christensenellaceae and Christensenella are significantly correlated (rho=0.2314008, p-value=5.236e-15). Therefore, measurements of sequences that belong to members of the family Christensenellaceae are a good proxy for estimates of the abundance and relative abundance of members of the Christenenella genus.

These methods of treatment can further include a step of measuring the levels of bacteria of the genus Christensenella, or the levels of Christensenellaceae, in a sample from the subject subsequent to administration of the composition, and continuing administration of the composition until the levels of Christensenella bacteria, or the levels of Christensenellaceae in the biological sample from said subject reach threshold levels. Threshold levels for Christensenella are $4.8 \times 10^{-3}$% of the total bacteria in the sample. Threshold levels for Christensenellaceae are 1.0% of the total bacteria in the sample.

It is appreciated that, for most individuals, there is no magic "weight loss pill". Rather, an overweight or obese subject must engage in a therapeutic regime that includes at least a reduced intake of calories and increased exercise. It is believed that altering the gastrointestinal environment of a subject by administration of the disclosed compositions can help an individual achieve weight loss goals, and/or prevent further weight gain, by altering the composition of the gut microbiome in favor of bacteria that are associated with a healthy BMI of less than 25.

The present disclosure is further illustrated by the following non-limiting examples.

EXAMPLES

Example 1. Materials and Methods

Sample Collection.

All work involving human subjects was approved by the Cornell University IRB (Protocol ID 1108002388). Fecal samples were collected at home by participants in the United Kingdom Adult Twin Registry (TwinsUK) in 15 ml conical tubes and refrigerated for 1-2 days prior to the participants' annual clinical visits at King's College London (KCL). Upon arrival at KCL, the samples were stored at −80° C. and shipped by courier on dry ice to Cornell University, where they were stored at −80° C. until processing.

Twin Dataset.

The inventors obtained 1,081 fecal samples from 977 individuals: 171 MZ and 245 DZ twin pairs, 2 from twin pairs with unknown zygosity, and 143 samples from just one twin within a twinship (i.e., unrelated). In addition, the inventors collected longitudinal samples from 98 of these individuals. Most subjects were female, ranging in age from 23 to 86 years (average age: 60.6±0.3 years). The average BMI of the subjects was 26.25 (±0.16) with the following distribution: 433 subjects had a low to normal BMI (<25), 322 had an overweight BMI (25-30), 183 were obese (>30) and 39 individuals in which the current BMI status was unknown.

DNA Extraction, Amplicon Generation and Sequencing.

Genomic DNA was isolated from an aliquot of ~100 mg from each sample using the POWERSOIL®-htp DNA isolation kit (MoBio Laboratories Ltd, Carlsbad, Calif.). 16S rRNA genes were amplified by PCR from each of the 1,081 samples (245 DZ twin pairs, 171 MZ twin pairs, 2 twin pairs with no zygosity status reported, 143 unrelated individuals, and 98 samples taken from individuals at a second, and for six individuals, a third time point) using the 515F and 806R primers for the V4 hypervariable region as previously described (Caporaso et al., 2011). PCR reactions, carried out in duplicate, consisted of 2.5 U EASY-A high-fidelity enzyme, 1× buffer (Stratagene, La Jolla, Calif.), 10-100 ng DNA template, and 0.05 µM of each primer. Reaction conditions consisted of initial denaturation at 94° C. for 3 min followed by 25 cycles of denaturation at 94° C. for 45 s, annealing at 50° C. for 60 s, extension at 72° C. for 90 s, and a final extension at 72° C. for 10 min. The replicate PCR reactions were combined and purified using a magnetic bead system (MAG-BIND® EZPURE, Omega Bio-Tek, Norcross, Ga.). PCR amplicons were quantified using the QUANTI-T PICOGREEN dsDNA Assay Kit (Invitrogen, Carlsbad, Calif.). Aliquots of amplicons (at equal masses) were combined for a final concentration of approximately 15 ng/µl. DNA was sequenced using the Illumina MISEQ 2×250 bp platform at Cornell Biotechnology Resource Center Genomics Facility. The inventors performed quality filtering and analysis of the 16S rRNA gene sequence data with QIIME 1.7.0 (Caporaso et al., *Nature Methods* 7:335-336 (2010)).

Heritability Calculations.

Heritability estimates were calculated on the OTU abundances, taxon bins, nodes throughout the bacterial phylogenetic tree, α-diversity, and PICRUSt-predicted COGs using the structural equation modeling software OpenMx (Boker, S., et al. Psychometrika 76, 306-317 (2011)).

Association of Traits with BMI.

The inventors compared microbiotas of high-BMI (BMI>30) to low-BMI (BMI<25) individuals to determine which taxa were enriched or depleted in the each group. For each of the traits (residuals after regression of covariates, described above) the inventors performed a t-test. P values were corrected for multiple testing using the Benjamini-Hochberg algorithm in R.

Using BMI as a Covariate in Heritability Analysis.

Since obesity has been shown to impact the composition of the microbiota, the inventors reran the heritability analysis on the taxa including BMI as an additional covariate. The inventors found a highly significant Pearson's correlation coefficient of 0.93 between the estimates with and without BMI as a covariate. The most highly heritable traits (specifically the Christensenellaceae) maintained the high heritability with the addition of BMI as a covariate. This analysis indicates that host genotype impacts the composition of the gut microbiome over and above what can be attributed to host BMI. However, the inventors note that host genetics may impact BMI through interactions with the microbiota.

PICRUSt.

PICRUSt v1.0.0 was used to predict abundances of COGs from the OTU abundances rarefied at 10,000 sequences per sample.

Animal Experiments.

All animal experimental procedures were reviewed and approved by the Institutional Animal Care and Usage Committee of Cornell University. Six-week old germ-free (GF) Swiss Webster mice were purchased from Taconic Farms Inc. (Hudson, N.Y.). None of the Taconic mice used were siblings, and there is a low probability of any cousins used within a study.

Fecal Transplants from Lean and Obese TwinsUK Donors.

Stool samples that were termed methanogen-positive contained approximately 0.2-10% of sequence reads that corresponded to methanogenic archaea. Stool samples that had no detectable methanogen sequences were considered methanogen-negative. Under anaerobic conditions in an anoxic glove box (Coy Lab Products, Grass Lake, Mich.), approximately 1 g of stool was resuspended in 15 ml of anaerobic PBS that contained 2 mM DTT as a reducing agent. Each stool sample was vortexed for 5 min, removed from the anaerobic chamber, and then immediately used. In the initial experiment, the inventors randomly assigned 21(14 male, 7 female) 6-week-old Swiss Webster germfree mice (Taconic Farms) to one donor each such that initial mouse mean weights were equivalent between treatment groups. Immediately prior to inoculation, the stool suspension was inverted 3 times and 500 µl were drawn up into a syringe fitted with a 20G gavage needle; 300 µl were stored for subsequent DNA extraction and analysis, whereas the remaining 200 µl was immediately inoculated into the recipient mouse via oral gavage. Fecal material from each donor was orally administered by gavage to 6-week old germ-free Swiss Webster mice in a 1:1 donor:mouse ratio. Mice were single-housed, kept under a 12-hour light/dark cycle, and fed an autoclaved 7017 NIH-31 mouse diet produced by Harlan Teklad (Madison, Wis.) ad libitum. Body weight and chow consumption were monitored weekly, where chow was measured before and after cage changes. Chow consumption rates were not different between treatment groups. A single mouse that had no remaining food in the cage at day 19 and weight loss was removed from any analysis at day 19. Stool samples were harvested weekly and immediately placed on dry ice.

The inventors replicated the experiment using stool samples from a set of 21 new donors, chosen similarly (by BMI and methanogen carriage). Again, 21 mice (female 6-week-old Swiss Webster germfree mice) were each assigned to a unique donor. Over the duration of the replication 3 mice died and were excluded from the dataset, leaving 5 L+, 4 L−, 3 O+, and 5 O− recipient mice. Sample collection and weight measurement were performed 20 hr, 5 days, and 10 days after inoculation as described above.

Fecal Transplants of *C. minuta* Amended Microbiome.

This experiment was similar to the obese/lean transfer described above, except for the following differences: (i) all mice were female (n=24) and housed 4 per cage, with 3 cages per treatment; (ii) a single obese subject was selected as the donor based on a lack of OTUs mapping to *Christensenella* (i.e., no OTUs identified as *Christensenella* out of 478,633 sequences obtained for that sample when the inoculum used in the transplant was sequenced) and lack of methanogens. *C. minuta* (purchased from DSMZ—German Collection of Microorganisms and Cell Cultures, Germany, DSM Strain No. 22607) was grown in brain heart infusion broth supplemented with yeast (5 g/l), menadione (1 mg/l), hemin (10 mg/l), and L-cysteine-HCL (0.5 g/l) at 37° C. under anaerobic conditions. Stool suspensions were prepared as above, with the exception that the mice receiving *C. minuta* were given an inoculum containing an addition of approximately $1 \times 10^8$ *C. minuta* cells, and the donor stool lacking *C. minuta* was amended with the same volume of PBS as a vehicle control.

The second *C. minuta* addition experiment was similar to the first, but had 21 mice that were divided into 3 treatments: "minus *C. minuta*", "plus *C. minuta*", and "plus heat-killed *C. minuta*". The minus and plus *C. minuta* samples were prepared as described in the first experiment. To prepare the heat-killed *C. minuta* inoculum, the culture was autoclaved for 20 minutes, and the donor stool was amended to contain approximately $1 \times 10^8$ *C. minuta* heat-killed cells. There were 7 mice per treatment group and mice were divided into 2 cages per treatment, one containing 3 mice and the other cage containing 4.

The third *C. minuta* addition experiment also contained 21 mice, with 10 mice receiving an inoculum of donor stool amended with heat-killed *C. minuta* that was prepared as described above, and 11 mice receiving donor stool amended with live *C. minuta*, prepared as above. Mice were housed 2 per cage (within the same treatment group), with the exception that one of the plus *C. minuta* cages contained 3 mice.

Percent Body Fat, Total Energy and Free Short Chain Fatty Acid (SCFA) Measurements.

Directly after euthanasia, mice were scanned by DEXA (Lunar PIXImus Mouse, GE Medical Systems, Waukesha, Wis.) to determine percent body fat. Gross energy content of mouse stool samples was measured by bomb calorimetry using an IKA C2000 calorimeter (Dairy One, Ithaca, N.Y.). Wet cecal contents were weighed and resuspended in 2% (v/v) formic acid by vortexing. The sample was centrifuged at 15,000 rpm for 5 min and the resulting supernatant was syringe filtered using a 0.22 µm filter to remove solids. One µl was injected into the gas chromatograph (HP series 6890) with a flame ionization detector. The temperatures of the injector and detector were 200° C. and 275° C., respectively. The column temperature was increased from 70° C. to 200° C. at a rate of 12° C./min. SCFAs were separated using a NUKOL™ capillary column (fused silica, 15 m×0.53 mm×0.5 µm, Supelco), using helium as the carrier gas at 21.4 ml/min.

Mouse Recipient Fecal and Cecal Bacterial Diversity.

DNA was extracted from frozen mouse cecal and fecal pellets, and from aliquots of the gavage preparation (inoculum), as described above. 16S rRNA gene sequences were obtained by PCR, sequenced, and analyzed as described above. Data for the obese/lean donor transplant experiments were rarefied to 55,000 sequences per sample, and data for the *Christensenella* addition experiments were rarefied to 11,228 sequences per sample.

Example 2. Heritability and Association Studies Identify Christensenellaceae as a Microbiome Family that Positively Correlates with Low BMI Microbiome Composition and Richness—

The inventors sorted sequences into 9,646 operational taxonomic units (OTUs, ≥97% ID). Of these OTUs, 768 were present in at least 50% of the samples. Taxonomic classification revealed a fairly typical Western diversity profile: the dominant bacterial phyla were Firmicutes (53.9% of total sequences), Bacteroidetes (35.3%), Proteobacteria (4.5%), with Verrucomicrobia, Actinobacteria, and Tenericutes each comprising 2% of the sequences, and a tail of rare bacterial phyla that together accounted for the remaining 1% of the sequences.

Christensenellaceae Associates with a Low BMI—

The family Christensenellaceae was significantly enriched in subjects with a lean BMI (<25) compared to those with an obese BMI (>30; Benjamini-Hochberg corrected P value <0.05 from t-test on transformed counts). Other members of the Christensenellaceae consortium were also enriched in lean-BMI subjects: the Dehalobacteriaceae, SHA-98, RF39, and the Methanobacteriaceae (FIG. 1B). Overall, a majority (n=35) of the OTUs with highest heritability scores (A>0.2, nominal P<0.05) were enriched in the lean subjects. A subset of OTUs classified as *Oscillospira* were enriched in lean subjects, and *M. smithii*, though not significantly heritable, was positively associated with a lean BMI.

Christensenellaceae is Associated with Health in Published Datasets—

Because the names *Christensenella* and Christensenellaceae were only recently assigned to the bacterial phylogeny, the inventors assessed the abundances of sequences assigned to these taxa in previously published studies. This analysis revealed that members of the Christensenellaceae were enriched in fecal samples of healthy versus pediatric and young adult IBD patients (P<0.05) (Papa, E., et al. PLoS One 7:e39242 (2012)). Christensenellaceae were at greater abundance in lean-BMI compared to obese-BMI twins in the Turnbaugh dataset but the difference was not quite significant ('time-point 2' samples, P=0.07). In a case study of the development of an infant's gut microbiome (Koenig, J. E., et al. *Proc Natl Acad Sci USA* 108 (Suppl 1):4578-4585 (2011)), Christensenellaceae was present at 8.6% in the mother's stool at the time of birth, and at 20% in the infant's meconium. The inventors also noted that Christensenellaceae is enriched in omnivorous compared to herbivorous and carnivorous mammals (Muegge, B. D., et al. *Science* 332: 970-974 (2011)). However, the inventors did not find a relationship between Christensenellaceae and diet information in human studies.

Christensenellaceae is Associated with Reduced Weight Gain in Germfree Mice Inoculated with Lean and Obese Human Fecal Samples—

Methanogens co-occurred with Christensenellaceae in this study and have been linked to low BMI in previous studies. Because of this previous association with a low-BMI, the inventors wanted to ensure that methanogens were present in the Christensenellaceae consortium in an initial experiment exploring its effect on weight phenotypes. Therefore, the inventors selected 21 donors for fecal transfer to germfree mice based on BMI status (low or high) and presence or absence of the methanogen-Christensenellaceae consortium. Donors fell into one of four categories: lean with detectable methanogens (L+), lean without methanogens (L−), obese with methanogens (O+), or obese without methanogens (O−). The abundance of Christensenellaceae positively correlated with the abundance of methanogens in donor stool (rho=0.72, P=0.0002), indicating that methanogen abundance was a good proxy for the methanogen-Christensenellaceae consortium.

A 16S rRNA analysis of the fecal microbiomes before and after transfer to germfree mice showed that although members of the Christensenellaceae were present throughout the experiment in recipient mice (FIG. 2A), *M. smithii* was undetectable in the mouse fecal or cecal samples (the first sampling was at 20 hrs post-inoculation). At 20 hrs post-inoculation, the microbiota had shifted dramatically in diversity from the inoculation, but by Day 5 had shifted back partially and remained fairly stable through Day 21 (FIGS. 2B, 2C, 3A, 3B).

Figures 2A, 2B, 2C, 2D, 2E, 2F:
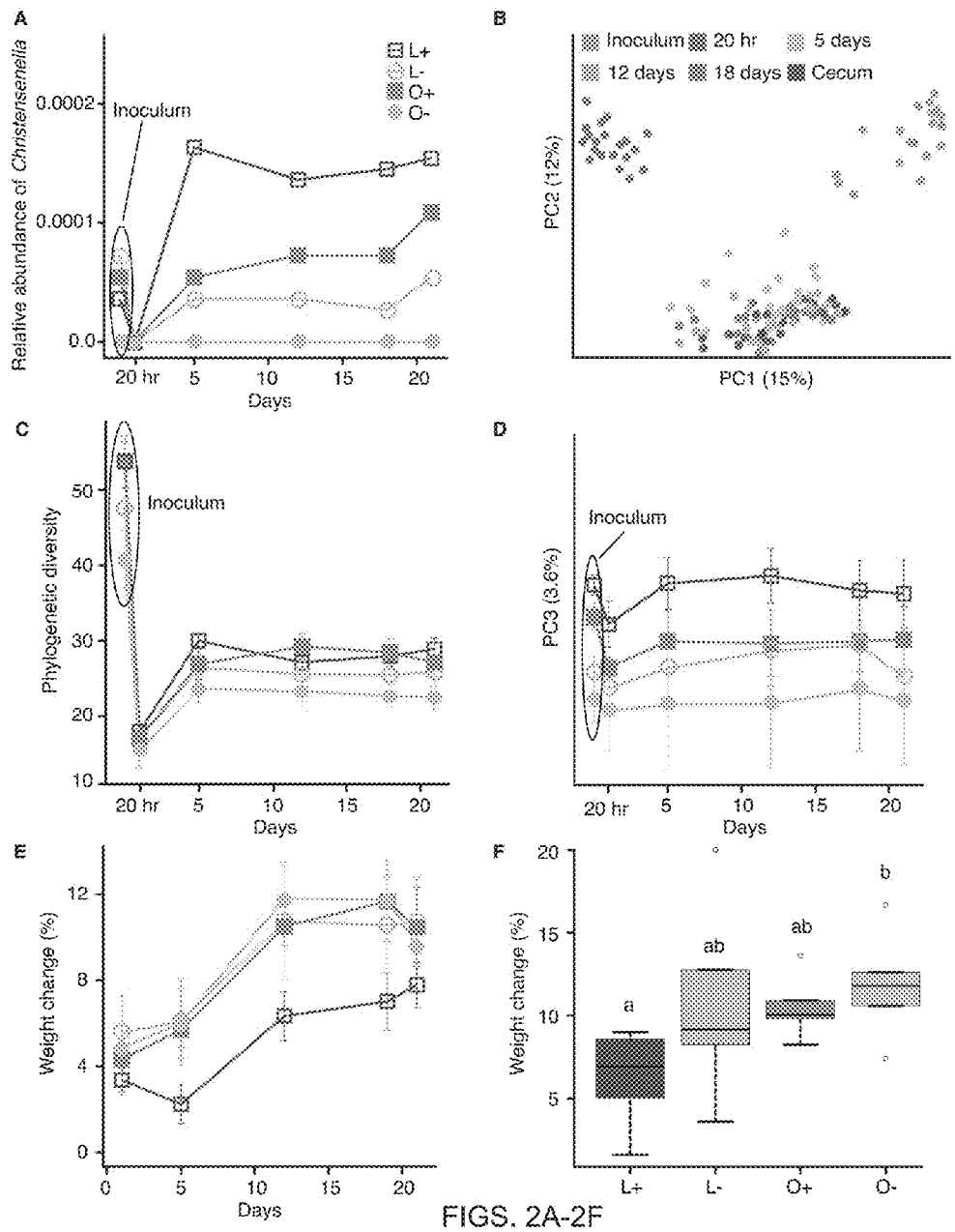
FIGS. 2A-2F. Fecal transplants from obese and lean UK Twins to germfree mice reveal levels of Christenenallaceae post-transfer mirror delayed weight gain. A: Median relative abundances for operational taxonomic units (OTUs) classified as the genus *Christensenella* in the four donor treatment groups over time in the recipient mouse microbiotas. B: Principal coordinates (PC) analysis of unweighted UniFrac distances for (i) the inoculum prior to transplantation, (ii) fecal samples at 4 time points, and (iii) cecal samples at Day 21 post-transplant. The amount of variance described by the first two PCs is shown on the axes. After gavage there is an initial selection event that occurs in the mouse, resulting in a large shift in the microbiome composition. This shift is illustrated by later time points being positioned in a different part of the graph, separate from the points that represent the inoculum from the 20 hr post gavage samples. By 5 days post gavage and later, the mouse microbiome has stabilized, as evidence on the graph by their repositioning relative to the other points. C: Richness (Faith's PD) for the microbiomes of the transplant mice plotted against time (days post inoculation, with Day 0=inoculation day). D: The mean values±S.E.M. for PC3 derived for the same analysis as shown in panel B are plotted against time (Day 0=inoculation day) for the four treatment groups. The amount of variance explained by PC3 is in parentheses. PC3 tracks with the separation between the methanogen positive and methanogen negative donors, and mirrors the weight gain phenotype observed in the mice recipients. E: Percent weight change since inoculation for germfree mouse recipients of 21 donor stools that were obtained from lean or obese donors with or without detectable *M. smithii*, which was used as a marker for the Christensenellaceae consortium. Means for each treatment group are plotted ±S. E. M. F: Box plots for percent weight changes for the 4 groups at Day 12 post-transplant, when maximal weight differences were observed. Letters next to boxes indicate significant differences if letters are different (p<0.05). For all panels, Dark blue=L+, lean donor with methanogens; Light blue=L−, lean donor lacking methanogens; Dark orange=O+, obese donor with methanogens; Light orange=O−, obese donor without methanogens. The inventors repeated this experiment with a set of 21 new mice and unique human donors and recovered the same effect.

The inventors applied principal coordinates analysis (PCoA) to analyze differences in the microbiomes between the treated animals. PCoA is an Ordination technique that reduces the dimensionality of the microbiome data set so that a summary of the between sample relationships can be visualized. The principal coordinates (PCs), each of which explains a certain fraction of the variability observed in the data set, are plotted. In the PCoA plots of FIGS. 2-5, each point represents a gut microbial community as characterized by a set of 16S rRNA gene sequences. Points that are closer together represent microbial communities that are more similar in sequence composition. The inventors determined that the abundances of *Christensenella* were correlated with PC3 (abundances rarefied at 55,000 sequences per sample vs. unweighted UniFrac; Spearman rho=0.59, $P<2.2\times10^{-16}$), and PC3 captured the differences between the 4 donor groups (FIG. 2D).

Figures 3A, 3B, 3C, 3D, 3E:
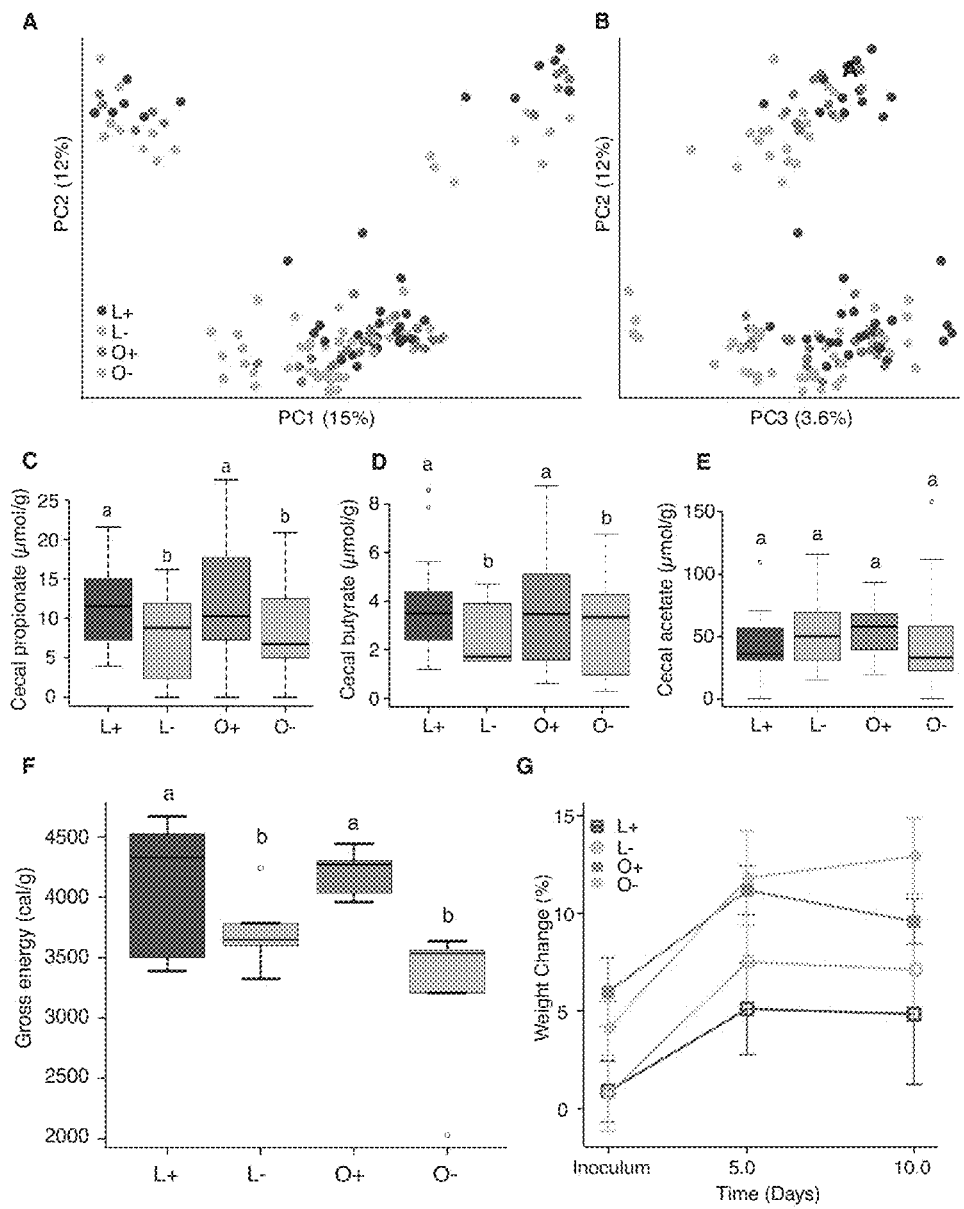

The inventors observed a trend for *Christensenella* abundances as highest in the L+ group and lowest in the O− group (FIG. 2A), which mirrored the weight differences between those groups: the percent change in body weights of the recipient mice was significantly lower in the L+ group compared to the O− group (Day 12, P<0.05, t-test; FIGS. 2E-2F). Cecal levels of propionate and butyrate were significantly elevated in mice receiving methanogen-positive compared to methanogen-negative microbiomes, controlling for the effect of donor BMI (two-way ANOVA, P<0.05 for both SCFAs, FIGS. 3C-3E). Stool energy content was significantly higher for the methanogen-positive microbiomes at Day 12, when the percent changes in weight were greatest (two-way ANOVA, P=0.004, no effect of BMI or interaction; FIG. 3F). In a replicated experiment, using 21 new donors, the same weight differences were observed (a significantly lower mean weight gain for the L+ compared to the O− mouse recipients at Day 10 post-inoculation; one-way t-test, P=0.047; FIG. 3G).

Example 3. Administration of *Christensenella* Inhibits Weight and Adiposity Gains

*Christensenella minuta* Added to Donor Stool Reduces Adiposity Gains in Recipient Mice.

Based on the observation that *Christensenella* levels in the previous experiment were similar to the weight gain patterns, the inventors performed experiments in which a donor stool lacking detectable *Christensenella* was amended with *C. minuta* and weight gain of recipient mice was monitored. One obese human donor was selected from the 21 donors from the first transplant experiment based on its lack of detectable OTUs assigned to the genus *Christensenella*. At Day 21 post-gavage, mice receiving the *C. minuta* treatment weighed significantly less than those that received unamended stool (nested ANOVA, P<0.05, FIG. 4A). Adiposity was significantly lower for mice receiving the *C. minuta* treatment (nested ANOVA, P=9.4×10$^{-5}$, FIG. 4B). Energy content for stool collected at Day 21 was not different between treatments.

Figures 4A, 4B, 4C, 4D, 4E:
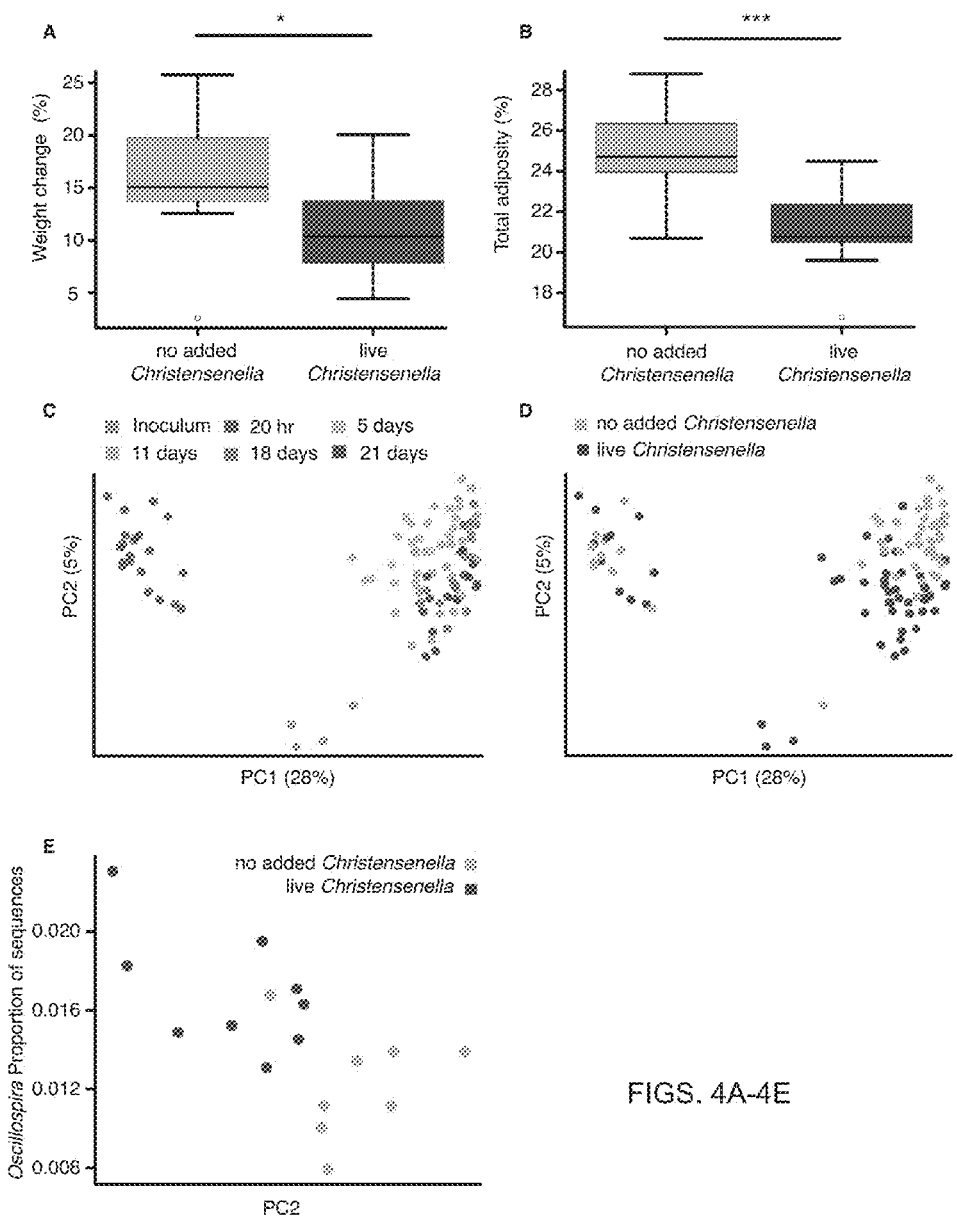
FIGS. 4A-4E. Addition of *Christensenella minata* to donor stool leads to reduced weight and adiposity gains in recipient mice. A: Box plot of percent weight change for germfree mouse recipients of a single donor stool only (lacking detectable *Christensenella* in unrarefied 16S rRNA data) or the donor stool amended with live *C. minuta*. B: Box plots showing percent body fat for mice in each group at Day 21 N=12 mice per treatment. C, D: Principal coordinates analysis (PCoA) of unweighted UniFrac distances for (i) the inoculum prior to transplantation, (ii) fecal samples at 5 time points post-transplant; see panel legend for color key. The amount of variance described by the first two PCs is shown on the axes. Variation between samples along PC1 is driven by the changes in the microbiome over time and variation between samples along PC2 reflects the changes in the microbiome after the addition of *C. minuta*. The same data projection is shown in panels C and D; sample symbols are colored by time point (C) and by treatment (D). E: Relationship between PCs from the PCoA analysis and levels of *Oscillospira* at Day 21 (rho=−0.71, P=P<0.001). Symbols are colored by treatment.
Figures 5A, 5B, 5C, 5D, 5E:
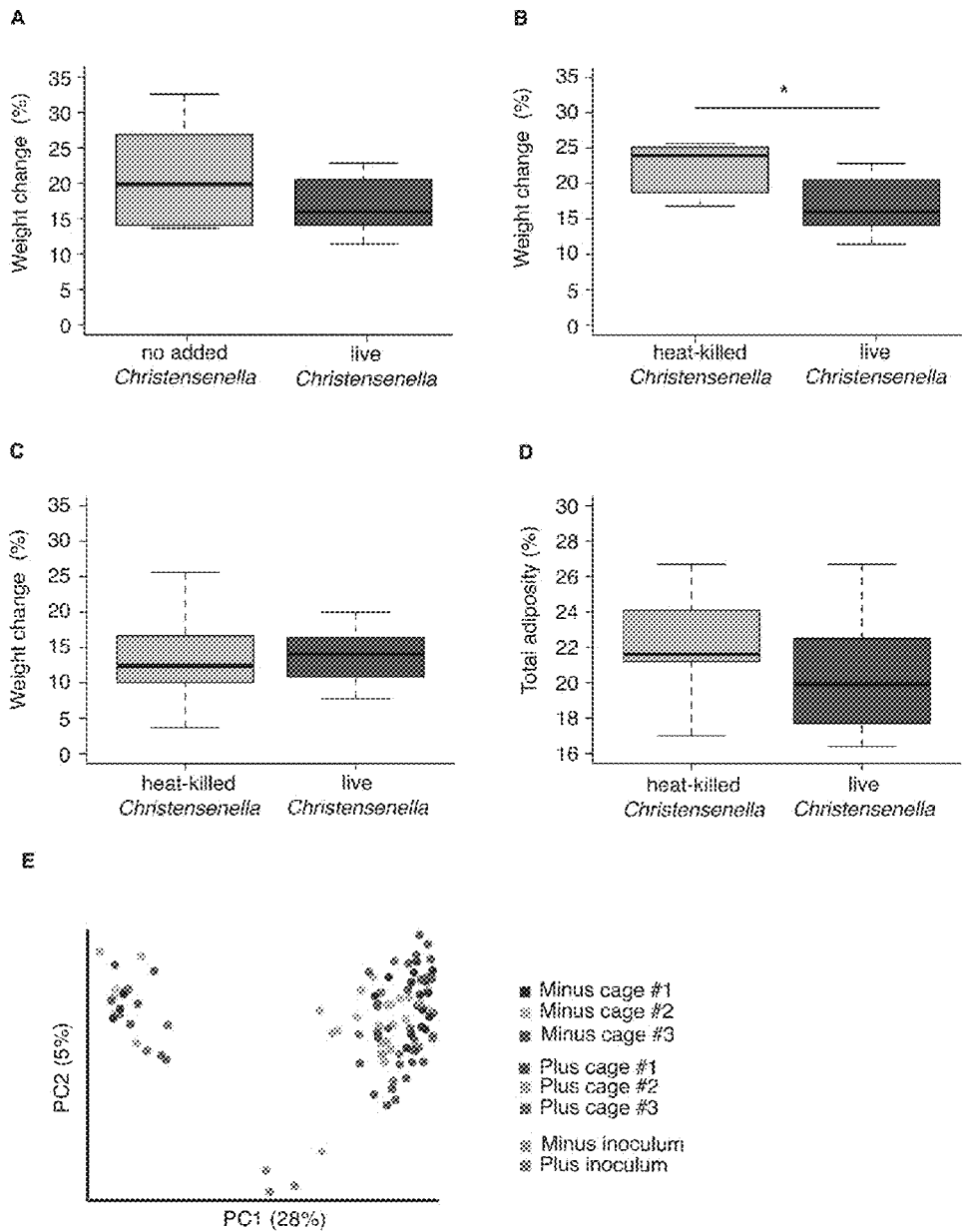
FIGS. 5A-5E: Phenotype effects of *Christensenella* addition. A-B: First repeat of the addition experiment. C-D: Second repeat of the addition experiment. Panels A and B are box plots that show percent weight change at day 23 relative to the starting mouse weight for 6-wk old Swiss-Webster germfree mice inoculated with stool from an obese donor lacking *Christensenella* with vehicle control versus live *C. minuta* addition (A) or heat-killed control versus *C. minuta* addition (B). Note that the live *C. minuta* data are the same data represented in both panels A and B. A second repeat (third iteration) of the experiment is shown in panels C and D, which show the relative weight change at day 21(C) and total adiposity of mice at day 21(D). N=7-11 mice per treatment. Panel E shows the PCoA plot of the unweighted UniFrac distances for the 16S rRNA analysis of samples derived from the first *C. minuta* addition experiment. Both the donor inoculum and 5 time points from mouse stool are shown. Symbols are colored by cage to show the co-caging of the mice.

Analysis of the microbial community by 16S rRNA amplicon sequencing showed an impact on the overall community diversity that persisted over time (FIG. 4C). After an initial acclimation (20 h), the communities within recipient mice began to separate by treatment regardless of the effects of time and co-caging (FIGS. 4C-4D; FIG. 5). As shown in FIG. 4D, PC2 shows a clustering effect of samples based on treatment group, showing that the addition of *Christensenella* accounts for approximately 5% of the variation of taxa between samples. The greatest separation of samples is at day 21, which is the far right of this plot. The inventors determined that two taxa, the genus *Oscillospira* and the family Erysipelotrichaceae are significantly different between treatment groups. The former is at a higher abundance in the CM+ mice, and also significantly correlates with PC2. Erysipelotrichaceae is depleted in the CM+ mice. At 5 days post-inoculation, the relative abundance of *C. minuta* was similar to that observed in the previous transplant experiment and persisted throughout the duration of the study. *Oscillospira* abundances were significantly correlated with PC2 in the unweighted UniFrac analysis of the communities (rho=−0.71, P=0.0009; FIG. 4E), which is the PC that separates the *C. minuta*-amended and unamended microbiotas.

The inventors' transplantation experiments showed a moderating effect of methanogen-presence in the human donor on weight gain of recipient mice, although strikingly, *M. smithii* did not persist in mice. In contrast, Christensenellaceae levels in mice mirrored their weight gain. Transfer to germfree mice of microbiomes from obese and lean donors generally results in greater adiposity gains for obese compared to lean donors. However, studies have not reported the methanogen or Christensenellaceae status of lean or obese donors, so whether these microbes affect the host phenotype is unknown. *M. smithii* has been associated with a lean phenotype in multiple studies, raising the possibility that methanogens are key components of the consortium for regulating host phenotype. The results of the inventors' methanogen-Christensenellaceae transfer revealed that although methanogens may be a marker for a low BMI in humans, they are not required to promote a lean phenotype in the germfree mouse experimental model. This result suggests that methanogens may be functionally replaced by another consortium member in the mouse, while the Christensenellaceae are not.

The results of the *C. minuta* addition supported the hypothesis that members of the Christensenellaceae promote a lean host phenotype. Addition of *C. minuta* also remodeled the diversity of the community. Intriguingly, *Oscillospira*, which includes heritable OTUs in the TwinsUK dataset and is associated with a lean BMI, was enriched in the *C. minuta*-amended microbiomes. How *C. minuta* reshapes the community remains to be explored. The relatively low levels of *C. minuta* and its profound effects on the community and the host may indicate that it is a keystone taxon. Together these findings indicate that the Christensenellaceae are highly heritable bacteria that can directly contribute to the host phenotype with which they associate.

What is claimed is:

1. A method of inhibiting weight gain, promoting weight loss, or reducing adiposity in a mammalian subject in need, comprising oral administration of an effective amount of a composition comprising substantially purified *Christensenella minuta* bacteria wherein at least 50% of the *Christensenella minuta* in said composition are viable.

2. The method of claim 1, wherein the *Christensenella minuta* bacteria are lyophilized.

3. The method of claim 1, wherein $10^6$ to $10^{12}$ colony forming units (CFUs) of the *Christensenella minuta* bacteria are present in the composition.

4. The method of claim 3, wherein $10^8$ to $10^{11}$ colony forming units (CFUs) of the *Christensenella minuta* bacteria are present in the composition.

5. The method of claim 1, wherein said administration increases the levels of the *Christensenella minuta* bacteria relative to the levels of other bacteria in the gastrointestinal tract of said subject.

6. The method of claim 1, wherein said administration comprises administration on a daily or weekly basis.

7. The method of claim 1, wherein said subject is overweight, has obesity, has metabolic syndrome, and/or has diabetes.

8. The method of claim 1, wherein the composition is formulated as a food or drink.

9. The method of claim 1, wherein said subject is human.

10. A method of inhibiting weight gain, promoting weight loss, or reducing adiposity in a mammalian subject in need, comprising oral administration of a composition comprising $10^6$ to $10^{12}$ colony forming units (CFUs) of substantially purified *Christensenella minuta* bacteria wherein at least 50% of the *Christensenella minuta* in said composition are viable and wherein said composition is administered in a single dose or is split into multiple doses.

11. The method of claim 10, wherein the *Christensenella minuta* bacteria are lyophilized.

12. The method of claim 10, wherein $10^8$ to $10^{11}$ colony forming units (CFUs) of the *Christensenella minuta* bacteria are present in the composition.

13. The method of claim 10, wherein said administration increases the levels of the *Christensenella minuta* bacteria relative to the levels of other bacteria in the gastrointestinal tract of said subject.

14. The method of claim 10, wherein said administration comprises administration on a daily or weekly basis.

15. The method of claim 10, wherein said subject is overweight, has obesity, has metabolic syndrome, and/or has diabetes.

16. The method of claim 10, wherein the composition is formulated as a food or drink.

17. The method of claim 10, wherein said subject is human.

* * * * *